US009243047B2

(12) United States Patent
Del Campo Ascarateil et al.

(10) Patent No.: US 9,243,047 B2
(45) Date of Patent: Jan. 26, 2016

(54) INFLUENZA NUCLEOPROTEIN VACCINES

(71) Applicant: Imaxio, Paris (FR)

(72) Inventors: Judith Del Campo Ascarateil, Taverny (FR); Fergal Hill, Lyons (FR)

(73) Assignee: Imaxio (FR)

( * ) Notice: Subject to any disclaimer, the term of this patent is extended or adjusted under 35 U.S.C. 154(b) by 0 days.

(21) Appl. No.: 14/570,155

(22) Filed: Dec. 15, 2014

(65) Prior Publication Data
US 2015/0098958 A1    Apr. 9, 2015

Related U.S. Application Data

(63) Continuation of application No. PCT/EP2014/055438, filed on Mar. 18, 2014.

(30) Foreign Application Priority Data

Mar. 18, 2013    (EP) .................................... 13305320

(51) Int. Cl.
| | | |
|---|---|---|
| C07K 14/47 | (2006.01) | |
| C07K 14/005 | (2006.01) | |
| A61K 47/48 | (2006.01) | |
| C07K 14/435 | (2006.01) | |
| C07K 14/445 | (2006.01) | |

(52) U.S. Cl.
CPC ............. *C07K 14/47* (2013.01); *A61K 47/4833* (2013.01); *C07K 14/005* (2013.01); *C07K 14/435* (2013.01); *C07K 14/445* (2013.01)

(58) Field of Classification Search
None
See application file for complete search history.

(56) References Cited

U.S. PATENT DOCUMENTS 8,815,812 B2 *   8/2014   Mattsby-Baltzer et al. . 514/21.3

FOREIGN PATENT DOCUMENTS

| WO | 2005/014654 A2 | 2/2005 |
| WO | 2007/062819 A2 | 6/2007 |
| WO | 2011/045612 A1 | 4/2011 |
| WO | WO 2014/090905 A1 * | 6/2014 |

OTHER PUBLICATIONS

Ye et al., Nature, 2006, 444:1078-1082.*
Jun. 23, 2014 (PCT) International Search Report—App PCT/EP2014/055438.
Ogun Solabomi A et al., "The oligormerization Domain of C4-Binding Protein (C4bp) Acts as an Adjuvant, and the Fusion Protein Comprised of the 19-Kilodalton Merozoite Surface Protein 1 Fused with the Murine C4bp Domain Protects Mice against Malaria," Infection and Immunity, American Society for Macrobiology, USA, vol. 76, No. 8, Aug. 1, 2008, pp. 3817-3823, XP009106276, ISSN: 0019-9567.
Spencer Alexandra J et al., "Fusion of the *Mycobacterium tuberculosis* Antigen 85A to an Oligomerization Domain Enhances Its Immunogenicity in Both Mice and Non-Human Primates," PLOS one, vol. 7, No. 3, Mar. 2012, XP002698954.
Kibler Karen V et al., "Polyarginine inhibiys gp160 processing by furin and suppresses productive human immunodeficiency virus type 1 infection," Journal of Biological Chemistry, vol. 279, No. 47, Nov. 19, 2004, pp. 49055-49063, XP002698955, ISSN: 0021-9258.
Smith J C et al., "Chemical synthesis and cloning of a poly(arginine)-coding gene fragment designed to aid polypeptide purification," Gene, Elsevier, Amsterdam, NL, vol. 32, No. 3, Dec. 1, 1984, pp. 321-327, XP025682441, ISSN: 0378-1119.
Kacprazak Magdalena M. et al., "Inhibition of furin by polyarginine-containing peptides-Nanomolar inhibition by NONA-D-arginine," Journal of Biological Chemistry, vol. 279, No. 35, Aug. 27, 2004, pp. 36788-36794, XP002698956, ISSN: 0021-9258.
A.D. Altstein et al., "Immunization with influenza A NP-expressing vaccinia virus recombinant protects mice against experimental infection with human and avian influenza viruses," Archives of Virology (2006) 151: 921-931.
Richard D. Antrobus et al., "A T Cell-Inducing Influenza Vaccine for the Elderly: Safety and Immunogenicity of MVA-NP +M1 in Adults Aged over 50 Years," PLOS One, Oct. 2012, vol. 7, Issue 10, pp. 1-10, www.plosone.org.
R. Arranz et al., "The Structure of Native Influenza Virion Ribonucleoproteins," Science 338, 1634 (2012), pp. 1634-1637.
M.F. Bachmann et al., "The Influence of Antigen Organization on B Cell Responsiveness," Science, vol. 262, Nov. 26, 1993, pp. 1448-1451.
Tamara K. Berthoud et al., "Potent CD8+ T-Cell Immunogenicity in Humans of a Novel Heterosubtypic Influenza A Vaccine, MVA-NP+M1," Clinical Infectious Diseases 2011;52(1): 1-7.
Amanda L. Blasius et al., "Intracellular Toll-like Receptors," Immunity 32, Mar. 26, 2010, pp. 305-315.
Robert B. Couch et al., "Prior Infections With Seasonal Influenza A/H1N1 Virus Reduced the Illness Severity and Epidemic Intensity of Pandemic H1N1 Influenza in Healthy Adults," Immunity to Pandemic Influenza in Adults, CID 2012:54 (Feb. 1) pp. 311-317.
Suzanne L. Epstein et al., "Vaccination with DNA encoding internal proteins of influenza virus does not require CD8+ cytotoxic T lymphocytes: either CD4+ or CD8+ T cells can promote survival and recovery after challenge," International Immunology, vol. 12, No. 1, pp. 91-101, (1999).
Susanne L. Epstein et al., "DNA Vaccine Expressing Conserved Influenza Virus Proteins Protective against H5N1 Challenge Infection in Mice," Emerging Infectious Diseases, vol. 8, No. 8, Aug. 2002, pp. 796-801.
Walters Fiers et al., "Soluble recombinant influenza vaccines," Phil. Trans. R. Soc. Lond. B (2001) 356, 1961-1963.
Ervin Fodor et al., "Rescue of Influenza A Virus from Recombinant DNA," Journal of Virology, Nov. 1999, p. 9679-9682, vol. 73, No. 11.
M. Gammelin et al., "Phylogenetic Analysis of Nucleoproteins Suggests That Human Influenza A Viruses Emerged from a 19th-Century Avain Ancestor," Mol. Biol. Evol. 7(2):194-200, 1990.

(Continued)

*Primary Examiner* — Stacy B Chen
(74) *Attorney, Agent, or Firm* — Banner & Witcoff, Ltd.

(57) ABSTRACT

The present invention is related to a fusion protein comprising a variant of a nucleoprotein antigen from Influenza strain A, B or C, and a variant of a C4bp oligomerization domain for increasing the cellular immunogenicity of the nucleoprotein antigen from Influenza. The invention is also related to nucleic acids, vectors, fusion proteins and immunogenic compositions, for their use as a vaccine or immunotherapy for the prevention and treatment of influenza disease.

15 Claims, 12 Drawing Sheets

(56) References Cited

OTHER PUBLICATIONS

M. Geiser et al., "Integration of PCR Fragments at Any Specific Site within Cloning Vectors without the Use of Restriction Enzymes and DNA Ligase," BioTechniques 31:88-92 (Jul. 2001).

O T Gorman et al., "Evolution of influenza A virus nucleoprotein genes: implications for the origins of H1N1 human and classical swine viruses," J. Virol. 1991, 65(7):3704.

John R. Greenland et al., "Chemical adjuvants for plasmid DNA vaccines," Vaccine, 25 (2007) 3731-374, www.elsevier.com/locate/vaccine.

C. Gschoesser et al., "CD4+ and CD8+ mediated cellular immune response to recombinant influenza nucleoprotein," Vaccine 20 (2002) 3731-3738.

B. Huang et al., "Influenza A virus nucleoprotein derived from *Escherichia coli* or recombinant vaccina (Tiantan) virus elicits robust cross-protection in mice," Virology Journal, 2012, 9:322.

Victor C. Huber et al., "Distinct Contributions of Vaccine-Induced Immunoglobulin G1 (IgG1) and IgG2a Antibodies to Protective Immunity against Influenza," Clinical and Vaccine Immunolgy, Sep. 2006, p. 981-990, vol. 13, No. 9.

Florian Krammer et al., Evaluation of the Influenza A Replicon for Transient Expression of Recombinant Proteins in Mammalian Cells,: Plos One, Oct. 2010, vol. 5, Issue 10, pp. 1-12.

Dominick J. Laddy et al., "Heterosubtypic Protection against Pathogenic Human and Avian Influenza Viruses via In Vivo Electroporation of Synthetic Consensus DNA Antigens," Plos One, Jun. 2008, vol. 3, Issue 6, pp. 1-8.

R A Lamb et al., "Orthomyxoviridae: the viruses and their replication," In: Knipe DM, Howley PM, editors., Fields Virology vol. 14th, ed. Philadelphia, PA, Lippincott Williams & Wilkins; 2001:1487-1531.

Patrick J. Lillie et al., "Preliminary Assessment of the Efficacy of a T-Cell-Based Influenza Vaccine, MVA-NP+M1, in Humans," Clinical Infectious Diseases 2012;55(1):19-25.

M. Luo et al., "Immunization with plasmid DNA encoding influenza A virus nucleoprotein fused to a tissue plasminogen activator signal sequence elicits immune responses and protection against H5N1 challenge in mice," Journal of Virological Methods 154 (2008) 121-127.

I. Mbawuike et al., "Humoral and cell-mediated immune responses of humans to inactivated influenza vaccine with or without QS21 adjuvant," Vaccine 25 (2007) 3263-3269.

A.J. McMichael et al., "Declining T-Cell Immunity to Influenza, 1977-82," The Lancet, Oct. 1, 1983, pp. 762-764.

Andrew J. McMichael et al., "Cytotoxic T-Cell Immunity to Influenza," The New England Journal of Medicine, vol. 309, No. 1, pp. 13-17 (1983b).

Andrew J. McMichael et al., "Recognition of Influenza A Virus Nucleoprotein by Human Cytotoxic T Lymphocytes," J. gen. Virol. (1986), 67, 719-726.

Arne Moeller et al., "Organization of the Influenza Virus Replication Machinery," Science 338, 1631-1634 (2012).

S. Nakada et al., "Complete nucleotide sequence of the influenza C/California/78 virus nucleoprotein gene," Virus Research, 1 (1984) 433-441.

Solabomi A. Ogun et al., "The Oligomerization Domain of C4-Binding Protein (C4bp) Acts as an Adjuvant, and the Fusion Protein Comprised of the 19-Kilodalton Merozoite Surface Protein 1 Fused with the Murine C4bp Domain Protects Mice against Malaria," Infection and Immunity, Aug. 2008, p. 3817-3823, vol. 76, No. 8.

Soumitra Roy et al., "Partial protection against H5N1 influenza in mice with a single does of a chimpanzee adenovirus vector expressing nucleoprotein," Vaccine 25 (2007) 684-6851.

M. Schotsaert et al., "Natural and long-lasting celluar immune responses against influenza in the M2e-immune host," Mucosal Immunology, vol. 6, No. 2, Mar. 2013, www.nature.com/mi.

Alexandra J. Spencer et al., "Fusion of the *Mycobacterium tuberculosis* Antigen 85A to an Oligomerization Domain Enhances Its Immunogenicity in Both Mice and Non-Human Primates," Plos One, Mar. 2012, vol. 7, Issue 3, pp. 1-11.

Z. Staneková et al., "Conserved epitopes of influenza A virus inducing protective immunity and their prospects for universal vaccine development," Virology Journal 2010, pp. 1-13.

Sean M. Sullivan et al., "Vaxfectin: a versatile adjuvant for plasmid DNA- and protein-based vaccines," Expert Opinion Drug Defiv, (2010) 7(12) pp. 1433-1446.

G. Sutter et al., "A recombinant vector derived from the host range-restricted and highly attenuated MVA strain of vaccinia virus stimulates protective immunity in mice to influenza virus," Vaccine 1994 vol. 12, No. 11, pp. 1032-1040.

B. Tarus et al., "Oligomerization paths of the nucleoprotein of influenza A virus," Biochimie 94 (2012) 776-785.

B. Tarus et al., "Molecular Dynamics Studies of the Nucleoprotein of Influenza A Virus: Role of the Protein Flexibility in RNA Binding," Plos One, Jan. 2012, vol. 7, Issue 1, pp. 1-9.

Paul G. Thomas et al., "Cell-mediated Protection in Influenza Infection," Emerging Infectious Diseases, www.cdc.gov/eid, vol. 12, No. 1, Jan. 2006.

Jeffrey B. Ulmer et al., "Heterologous Protection Against Influenza by Injection of DNA Encoding a Viral Protein," Science, vol. 259, Mar. 19, 1993, pp. 1745-1749.

David C. Wraith et al., "Purified Influenza Virus Nucleoprotein Protects Mice from Lethal Infection," j. gen. Virol. (1987), 68, 433-440.

J. Xu et al., "Evolutionary dynamics of influenza A nucleoprotein (NP) lineages revealed by large-scale sequence analyses," Infect Genet Evol. Dec. 2011; 11(8): 2125-2132.

Q. Ye et al., "Biochemical and Structural Evidence in Support of a Coherent Model for the Formation of the Double-Helical Influenza A Virus Ribonucleoprotein," Jan./Feb. 2013, vol. 4, Issue 1, pp. 1-10.

Q. Ye et al., "The mechanism by which influenza A virus nucleoprotein forms oligomers and binds RNA," Nature, vol. 444, Dec. 2006, pp. 1078-1082.

Jonathan W. Yewdell et al., "Influenza A virus nucleoprotein is a major target antigen for cross-reactive anti-influenza A virus cytotoxic T lymphocytes," Proc. Natl. Acad. Sci. USA, vol. 82, pp. 1785-1789, Mar. 1985.

Shizuo Akira et al., "Pathogen Recognition and Innate Immunity," Cell 124, 783-801, Feb. 24, 2006.

\* cited by examiner

INFLUENZA NUCLEOPROTEIN VACCINES

RELATED APPLICATION DATA

This application is a continuation of PCT application PCT/EP2014/055438 designating the United States and filed Mar. 18, 2014; which claims the benefit of EP application number 13305320.7 and filed Mar. 18, 2013 each of which are hereby incorporated by reference in their entireties.

BACKGROUND

A need exists for improved influenza vaccines. Current vaccine strategies against influenza focus on generating robust antibody (humoral) responses against hemagglutinins. Because of the high degree of antigenic drift among circulating influenza strains over the course of a year, vaccine strains must be reformulated specifically for each influenza season. Although annual (or seasonal) influenza vaccines are successful to varying degrees in different age categories, more effective protection is clearly needed particularly for the young and the elderly. Furthermore, there is a major, permanent risk that reassortant viruses will evolve which have acquired very different HA (hemagglutinin) genes in a process known as "antigenic shift". This would create a public health emergency, as current influenza vaccines rely essentially on the HA antigen.

Influenza is an enveloped, single-stranded, negative-sense RNA virus in the Orthomyxoviridae family of viruses, divided into 3 major types: A, B, and C. Influenza A viruses infect a wide variety of animals, including humans, birds, pigs, horses, bats and many others, although the tropism of any particular influenza virus is generally highly adapted to a particular host. Influenza B viruses infect a smaller number of species, namely humans and seals, but are still a substantial cause of annual influenza epidemics. Most human influenza infections are caused by influenza A or B; influenza C viruses, which infect humans and pigs, rarely account for serious human infections or epidemics (Lamb).

The current inactivated influenza virus vaccines induce antibodies that protect against closely related virus strains. Currently licensed vaccines mainly induce strain-specific neutralizing antibodies against hemagglutinin (HA), the main antigenic determinant on the surface of the virus, which is highly immunogenic, and can prevent disease caused by infection with a matching virus strain. However, HA has substantial antigenic variation which excludes its use alone in a vaccine designed to provide broad protection. For this reason, alternative vaccine strategies that generate protective responses directed against less variable targets are of great interest.

Natural infection with influenza A virus induces both humoral and cellular immunity. Long-lasting cellular immunity is directed predominantly against conserved, internal viral proteins, such as the nucleoprotein (NP). NP antigen is immunogenic in humans following natural infections, but the cytotoxic T lymphocytes that are induced have a short lifespan (McMichael a, McMichael b).

Cellular immunity against NP is valuable, as it is directed against different variants of NP epitopes, and NP-targeting DNA vaccines have induced cross-protective immunity in animals (Schotsaert).

The nucleoprotein (NP) antigen has long been recognized as a highly conserved antigen: even the most divergent influenza A strains share 90% identity in the NP proteins they encode (Gorman, Xu). Antigenic changes to NP are rare and only occur to a minor extent (Staneková).

PRIOR ART

Use of the Nucleoprotein as an Antigen in Vaccines

The use of influenza nucleoprotein as an antigen was described in the 1980s (Wraith). Cellular immune responses in mice against NP are capable of inducing immunity, and notably of producing cross-protection against divergent type A viruses. It was shown that immunization of mice with NP purified from a H3N2 virus could provide substantial protection (75%) from a lethal heterologous (H1N1) challenge, but it did not prevent infection.

DNA vaccines using the NP gene have been known for twenty years: they were used in the first "proof of concept" experiments for DNA vaccination itself (Ulmer).

The expression of NP from a viral vector was first demonstrated in the 1980s (Yewdell 1985), and immunization with this vector was associated with an improved generation of cytotoxic T lymphocytes against diverse influenza A, but not B, strains, in comparison with DNA vaccines. Since, it has been shown that immunization of mice with an MVA vector expressing the PR8 nucleoprotein protected them against low dose challenges by heterosubtypic influenza viruses (Altstein). More recently, a viral vector encoding the NP protein fused to the M1 protein has been used to immunize humans (Lillie, Berthoud, Antrobus). These studies showed notably that cellular immune responses to NP can be substantially boosted in older humans (Antrobus), when humoral responses are declining through immunosenescence.

Secretion of the Nucleoprotein

Some studies have suggested that the NP protein is primarily located in the nucleus, reducing the immunogenicity of such DNA vaccines (Staneková).

Improved cellular immune responses against NP can be obtained by forcing the secretion of NP, for example by fusing a tPA signal peptide to the NP gene (Luo), by formulation of the DNA (Greenland, Sullivan) and by the use of electroporation (Laddy) to improve DNA delivery.

Monomeric Influenza Nucleoproteins

The preferred use of monomeric antigens in fusion with C4bp oligomerisation domains was described in the patent application WO 2005/014654. But the risk in using monomerised antigens is their decreased immunogenicity. This was demonstrated by Bachmann and colleagues with the glycoprotein G of Vesicular Stomatitis Virus (Bachmann 1993), and for the influenza antigen Neuraminidase, or NA, by Fiers and colleagues (Fiers 2001). It is to be expected that decreasing or removing higher order structure from influenza nucleoproteins would decrease their immunogenicity.

A number of mutations have been shown to transform the influenza nucleoprotein, which naturally oligomerizes, into a monomeric form (Ye 2006). Monomeric versions of NP described in this 2006 paper were confirmed to be monomeric in more recent papers (Tarus, Ye 2012). The two point mutations described in these papers which render monomeric the nucleoprotein of influenza A, are conserved in the nucleoproteins of influenza B and C strains (see FIG. 3 in Nakada). Therefore the same point mutations could be introduced in nucleoproteins of influenza B and C strains, in order to render monomeric these other influenza nucleoproteins. But no studies of the immunogenicity of the monomeric nucleoproteins were carried out.

The major technical problem in preparing influenza vaccines with the NP antigen is inducing strong and durable cellular immune responses. The 'cellular immune response' is an immune response that does not involve antibodies but rather involves the activation of antigen-specific T-lymphocytes, and especially cytotoxic T lymphocytes, and the release of various cytokines in response to an antigen. CD4 cells or helper T cells provide protection against different pathogens by secreting cytokines that activate the immune response. Cytotoxic T cells (CD8) cause death by apoptosis of pathogens without using cytokines.

Although debate remains as to whether CD4 or CD8 responses against NP are more important for protection (Epstein), there is a consensus that cellular, rather than humoral, responses to the nucleoprotein are the key to the protection that this antigen can induce (Thomas). Vaccines that provide protection by eliciting a strong cytotoxic T cell response may be useful when T cell epitopes are derived from the highly conserved NP protein (Epstein; Roy). Cellular immune responses, mediated by T lymphocytes, mainly function by recognizing influenza virus-infected cells, by inhibiting viral replication and by accelerating virus clearance.

The specific T cells involved in conferring immunity include both CD4+ and CD8+ T cells, and often exert their functions through the action of secreted cytokines and cytolytic activity, respectively. Influenza NP-specific CD8+ CTL in particular could play important roles in heterosubtypic protective immunity against a lethal influenza virus challenge in mice (Gschoesser), including clearance of the influenza virus from the upper respiratory mucosal surfaces (Mbawuike), promoting survival and recovery after challenge (Epstein). An optimal NP-based vaccine would improve both CD4 and CD8 cellular responses.

This patent application provides methods for improving cellular immune responses to influenza virus nucleoproteins.

BRIEF DESCRIPTION OF THE INVENTION

The present invention is related to a method for increasing the immunogenicity, and particularly the cellular immunogenicity, of the NP antigens from Influenza viruses, by fusing at least one variant of the NP antigen from Influenza strains A, B or C to a variant of the chicken C4bp oligomerization domain as carrier protein.

The present invention is in particular related to a fusion protein, comprising at least one monomeric variant of the NP antigen from Influenza strain A, B or C, and a carrier protein IMX313 having the sequence as shown in SEQ ID NO: 1, such as described in the patent application WO2007/062819.

The present invention is in particular related to a fusion protein, comprising the monomeric variant of the NP antigen from Influenza strain A presenting the E339A and R416A point mutations as shown in SEQ ID NO: 2, and a variant of IMX313 carrier protein having a C-terminal substitution of at least one positively charged peptide having the sequence ZXBBBBZ wherein (i) Z is any amino acid or is absent, (ii) X is any amino acid and (iii) B is an arginine (R) or a lysine (K), as shown in SEQ ID NO: 3, such as described in the patent application PCT/EP2013/076289 filed on Dec. 11, 2013. A preferred variant of IMX313 carrier protein does not induce antibodies which cross-react with protamine.

The present invention is in particular related to a fusion protein, comprising a monomeric variant of the NP antigen, and a modified carrier protein IMX313T or IMX313P, as shown respectively in SEQ ID NO: 4 and SEQ ID NO: 5.

The present invention is also related to an immunogenic composition comprising a DNA sequence in a plasmid or a viral vector, further comprising a signal peptide, such as tPA, as shown in SEQ ID NO: 6.

The present invention is also related to a recombinant DNA sequence coding for said fusion proteins.

The present invention is also related to an immunogenic composition comprising a DNA sequence encoded by a plasmid or a viral vector, or a fusion protein, further comprising vaccine adjuvants or nucleic acid ligands for intracellular TLRs, as described in the patent application PCT/EP2013/076289 filed on Dec. 11, 2013.

The present invention is also related to a DNA plasmid, a viral vector, a fusion or an immunogenic composition, for its use as a vaccine or an immunotherapy as a method of prevention or treatment of the influenza.

DETAILED DESCRIPTION OF THE INVENTION

Before describing the present invention in detail, it is to be understood that this invention is not limited to particularly exemplified methods and may, of course, vary. In particular, the present invention is related to fusion proteins comprising at least one nucleoprotein antigen from Influenza, and is not limited to a specific influenza nucleoprotein.

All publications, patents and patent applications cited herein, whether supra or infra, are hereby incorporated by reference in their entirety. However, publications mentioned herein are cited for the purpose of describing and disclosing the protocols, reagents and vectors that are reported in the publications and that might be used in connection with the invention.

Furthermore, the practice of the present invention employs, unless otherwise indicated, conventional protein purification and molecular biological techniques within the skill of the art. Such techniques are well known to the skilled worker, and are explained fully in the literature. In the claims that follow and in the consecutive description of the invention, except where the context requires otherwise due to express language or necessary implication, the word "comprise", "contain", "involve" or "include" or variations such as "comprises", "comprising", "containing", "involved", "includes", "including" are used in an inclusive sense, i.e. to specify the presence of the stated features but not to preclude the presence or addition of further features in various embodiments of the invention.

The following terms are defined for a better understanding of the invention:

Influenza viruses are of three types, A, B and C. This classification was initially serological: antisera to the influenza virus A nucleoprotein cross-react with the nucleoprotein of other A class viruses, but not with those of B class or C class viruses. Influenza A viruses are further classified into subtypes, based on the serological cross-reaction of their hemagglutinin (H) and neuraminidase (N) glycoproteins.

By "Influenza nucleoproteins" are meant the nucleoproteins of all three types (A, B and C) of the Influenza viruses.

A "carrier protein" designates generally a protein to which antigens are conjugated or fused and thereby rendered more immunogenic. Here the term is used specifically in the meaning of a protein carrying an antigen. The function of the protein is to increase the immunogenicity of said antigen to which it is conjugated or fused.

A "variant of NP" designates all the proteins having a sequence with at least 90% of identity of the wild type version of influenza nucleoproteins from Influenza strains A, B and C.

A "variant of the chicken C4bp oligomerization domain" is a variant of the C4bp domain of the SEQ ID NO: 1 described in the patent applications WO2007/062819, and PCT/EP2013/076289 filed on Dec. 11, 2013, both references being incorporated herein by reference, particularly a fragment of at least 48 contiguous amino acids and/or having at least 70% amino acid sequence identity of said SEQ ID NO: 1 described in the patent applications WO2007/062819.

A "variant of IMX313 carrier protein" is described in the patent application PCT/EP2013/076289 filed on Dec. 11, 2013.

Protamine consists of a group of heterogenous peptides with an average molecular weight of 4500 Daltons, obtained from fish. Approximately 67% of the amino acid composition of protamine is arginine. It has long been used to formulate insulin (in Neutral Protamine Hagedorn), or to neutralize heparin.

The term "fusion protein" designates a recombinant protein, non-naturally existing, comprising two domains from different origins that have been fused. More precisely, in the invention, the fusion protein comprises an influenza nucleoprotein antigen fused to a carrier domain variant of the chicken C4bp oligomerization domain, particularly 'IMX313T' or 'IMX313P'. Fusion has the advantage of creating a homogenous product. More formally, the "conjugation" can be described as genetic: the DNA encoding the pro-immunogenic carrier protein is spliced to the DNA encoding the antigen. The antigen can be fused to the N- or C-terminal of the carrier protein.

The invention is related to an immunogenic composition, comprising at least one variant of an Influenza nucleoprotein antigen and a variant of a C4bp oligomerization domain, and eliciting a increased cellular immune response against the Influenza nucleoprotein antigen.

According to the present invention, the nucleoprotein fused to the carrier protein variant of the chicken C4bp oligomerization domain, particularly IMX313T or IMX313P, can be a nucleoprotein from any type (A, B or C) of the Influenza viruses.

The nucleoprotein antigen can be fused to the N- or C-terminal of the carrier protein, particularly IMX313T or IMX313P.

According to the invention, at least one nucleoprotein is fused to one carrier protein, particularly IMX313T or IMX313P; however, two or more nucleoproteins, identical or different, can be fused to the same carrier protein.

According to a preferred aspect of the invention, the nucleoprotein antigen fused to the variant of the chicken C4bp oligomerization domain, particularly IMX313T or IMX313P, is a monomeric antigen. Indeed, it is advantageous to use monomeric antigens, as described in the patent application WO 2005/014654, provided that monomerization does not diminish their immunogenicity. Moreover, NP forms a trimer in crystals (Ye 2006) and other oligomers in vivo (Arranz, Moeller). Fusion of a trimeric or oligomeric protein to a heptameric protein such as IMX313T or IMX313P risks the creation of steric clashes. On the other hand, monomeric forms of naturally oligomeric proteins have diminished immunogenicity (Fiers).

To obtain monomeric nucleoprotein antigen, the man skilled in the art knows different point mutations that can be introduced into the protein sequence of the NP antigen, to induce its monomerisation. In particular, the NP antigen presents at least one of the two following point mutations: E339A and R416A.

In an embodiment of the invention, the NP antigen is from the Influenza strain A.

In a preferred embodiment of the invention, the NP antigen comprises both point mutations E339A and R416A, and is therefore monomeric.

In another embodiment of the invention, the NP antigen presents the polypeptidic sequence as shown in SEQ ID NO: 2.

Increased cellular immune responses to antigens expressed from DNA vaccines have previously been obtained by fusing the gene of the antigen to a gene encoding the IMX313 (Spencer). Advantageously, variants of this domain presenting a C-terminal substitution of at least one positively charged peptide having the sequence ZXBBBBZ wherein (i) Z is any amino acid or is absent, (ii) X is any amino acid and (iii) B is an arginine (R) or a lysine (K), as shown in SEQ ID NO: 3, which enables an improved immune response to an antigen when fused to said antigen, such as described in the patent application PCT/EP2013/076289 filed on Dec. 11, 2013. A preferred variant of IMX313 carrier protein does not induce antibodies which cross-react with protamine.

Particular improved variants, called IMX313T and IMX313P, have been recently described in the patent application PCT/EP2013/076289 filed on Dec. 11, 2013. Their peptide sequences are the following:

```
                                          SEQ ID NO: 4
KKQGDADVCGEVAYIQSVVSDCHVPTAELRTLLEIRK-

LFLEIQKLKVELQSPRRRRS

SEQ ID NO: 5
KKQGDADVCGEVAYIQSVVSDCHVPTAELRTLLEIRK-

LFLEIQKLKVEGRRRRRS
```

In another embodiment of the invention, the fusion protein comprises a NP antigen which comprises a signal peptide. Several studies have suggested that the NP protein is primarily located in the nucleus, which could potentially reduce the immunogenicity of such DNA vaccines. Therefore, enabling the secretion of NP antigen, by adding a signal peptide, is desirable. In particular, said signal peptide is the tPA (tissue plasminogen activator) secretory signal peptide as described in (Luo).

In a specific embodiment of the invention, the NP antigen is monomeric and comprises a signal peptide.

In another embodiment of the invention, the NP antigen comprises both mutations E339A and R416A, and the signal peptide tPA. As shown in the examples, the fusion protein comprising IMX313T and the monomeric NP antigen comprising a signal peptide induces, when injected as a DNA vaccine in mice, a stronger Th1 response (IgG2a) than Th2 response (FIG. 13). The consensus among immunologists is that Th1 responses are preferable to Th2 responses. However methods for improving preferentially Th1 responses to an antigen, without the use of adjuvants developed for this purpose, are not known in the art. In the examples below, it is shown that the fusion of IMX313T or IMX313P to influenza nucleoprotein antigens preferentially improves Th1 responses.

The invention is also related to a fusion protein comprising any carrier protein comprising a coiled-coil domain, and at least one nucleoprotein (NP) antigen from Influenza. In particular, said nucleoprotein antigen is monomeric.

The present invention is also related to a nucleic acid encoding for a fusion protein such as described above, and in particular:
coding for a fusion protein comprising a NP antigen and IMX313T or IMX313P;
coding for a fusion protein comprising a monomeric NP antigen and IMX313T or IMX313P;

coding for a fusion protein comprising a NP antigen comprising a signal peptide and IMX313T or IMX313P;
coding for a fusion protein comprising a monomeric NP antigen comprising a signal peptide and IMX313T or IMX313P.

As preferred embodiments, said nucleic acid codes for a fusion protein comprising a monomeric NP antigen from Influenza A. As preferred embodiments, said nucleic acid codes for a fusion protein which does not induce antibodies cross-reacting with protamine. In particular, said nucleic acids present the sequences as shown in SEQ ID NO: 6 and SEQ ID NO: 7.

The present invention is also related to a vector comprising the nucleic acid presented above, and genetic elements such as promoters and enhancers to ensure the expression of the DNA cassette in host cells.

The present invention is also related to an immunogenic composition comprising:
a fusion protein or a nucleic acid or a vector as presented above, and
nucleic acid ligands for intracellular TLRs, and/or any other vaccine adjuvants.

Toll-Like Receptors (TLRs)

Cells of the innate immune system detect pathogens through a limited set of germ-line encoded receptors. These innate immune receptors recognize a series of conserved molecular structures expressed by pathogens, the PAMPs (pathogen associated molecular patterns).

These pathogen-derived molecules generally represent complex molecules that are very specific for a set of pathogens. TLRs represent a set of immune pattern recognition receptors able to alert the immune system immediately after infection by a pathogen. They play an important role as pivotal components between innate and adaptive immunity and are able to scent out many pathogens ranging from viruses to parasites. The first characterized TLR, called Toll, was shown to be responsible for anti-fungal responses in the adult *Drosophila* fly and 10 human equivalents involved in pathogen recognition have been identified to date. TLRs can be classified into different groups based on their localization and the type of PAMPs they recognize. TLRs 1, 2, 4, 5 and 6 are principally expressed on the cell surface, where they recognize mostly bacterial products, while TLRs 3, 7, 8 and 9 are localized in intracellular compartments and recognize mostly viral products and nucleic acids.

Intracellular Toll-Like Receptors

Besides, to improve methods of immunization, it is also of great importance to limit signaling through TLR receptors. Toll-like receptors (TLRs) are a class of protein that play a key role in the innate immune system. Once microbes have breached physical barriers of organisms, they are recognized by TLRs. The recognized features from microbes include double-stranded RNA of viruses, unmethylated CpG site islands of bacterial and viral, and certain RNA and DNA molecules.

There is substantial interest in such nucleic acids as they are ligands for a class of Toll-Like Receptors (hereafter TLRs), and notably for TLR3, TLR7, TLR8, TLR9 and TLR13 (Blasius and references therein). These are sometimes classed as the "Intracellular Toll-like Receptors", but at least TLR3 is also present on some cell surfaces. TLR3 is expressed on a variety of epithelial cells including airway, uterine, corneal, vaginal, cervical, biliary and intestinal epithelial cells, and these cells appear to express TLR3 on their cell surfaces (Akira).

The importance of limiting signaling through these receptors, and notably the TLR3 receptor, is dose-dependent. Binding nucleic acid ligands tightly to the antigen is thus essential, to prevent their binding to TLRs in the absence of the antigen. Tightly bound intracellular TLR ligands are therefore highly preferred over formulations in which binding is less tight. Therefore, the man skilled in the art is looking for antigenic compositions able to bind efficiently TLR ligands, so that they are not separated from the antigen before the antigen arrives in the cells where it will trigger an immune response, with the goal of diminishing the potential adverse effects mediated by the binding of the ligands to TLR receptors elsewhere.

In the present application, and in particular in examples, the following intracellular TLR ligands have been used:
For TLR3: poly I:C being a duplex of a polynucleotide of polyinosinic acid hybridized to polycytidylic acid, an analogue of double-stranded RNA. The chain length was twenty nucleotides for each strand.
For TLR7: an oligonucleotide, called ssRNA40, with the sequence 5' GsCsCsCsGsUsCsUsGsUsUsGsUsG-sUsGsAsCsUsC 3' where "s" represents a phosphothioate linkage (SEQ ID NO: 8);
For TLR9: an oligonucleotide called ODN1826 with the sequence: 5' tccatgacgttcctgacgtt 3' (SEQ ID NO: 9).

In a specific aspect of the invention, the immunogenic composition comprises:
a fusion protein or a nucleic acid or a vector as presented above, and
poly I:C.

The invention is also related to a fusion protein such as described above, for its use as a vaccine for the prevention and treatment of influenza disease. Said influenza vaccine can be used for multiple applications:
prevention of seasonal influenza;
prevention in a pandemic situation;
'universal' prevention, i.e. a vaccine immunizing against all types of influenza viruses;
immunotherapy of all types of influenza.

Methods of prevention or treatment of the influenza can be performed, with specific vaccines according to the invention, in human or animal bodies. The man skilled in the art knows how to adapt the compositions of vaccines for each specific application and specific patients.

The invention is also related to a nucleic acid such as described above, for its use as a DNA vaccine for the prevention of influenza disease.

The invention is also related to a vector such as described above, for its use as a viral vaccine for the prevention of influenza disease.

The invention is also related to an immunogenic composition such as described above for its use as a vaccine for the prevention of influenza disease.

The invention is also related to a method for increasing the cellular immune response to the nucleoprotein antigen of influenza, comprising the fusion of this antigen to a carrier protein IMX313T or IMX313P having the sequences as shown in SEQ ID NO: 4 and SEQ ID NO: 5.

In another embodiment of the invention, the fusion protein or the nucleic acid or the vector or the immunogenic composition such as described previously is used in immunotherapy of influenza disease.

DRAWINGS

FIG. 1: map of the parental plasmid pcDNA3 NP—This plasmid and its derivatives, constructed as described in the Examples, were used for DNA vaccination.

FIG. 2: Comparison of total T cells secreting IFN-γ in response to immunization with plasmids encoding NP, or NP fused to IMX313.

FIG. 3: Comparison of CD8 and CD4 T cells secreting IFN-γ in response to immunization with a plasmid encoding NP or a plasmid encoding NP fused to IMX313.

FIG. 4: Comparison of IgG antibody responses to recombinant NP induced by DNA plasmids encoding either NP or NP fused to IMX313

FIG. 5: Comparison of IgG antibody subclass responses to recombinant NP induced by DNA plasmids encoding either NP or NP fused to IMX313.

FIG. 6: Comparison of total T cell responses to plasmids encoding NP, monomeric NP (NPm), monomeric NP fused to IMX313 (NPm-IMX313) and monomeric NP fused to IMX313T (NPm-IMX313T).

FIG. 7: Comparison of CD8+ and CD4+ T cell responses to plasmids encoding NP, monomeric NP (NPm), monomeric NP fused to IMX313 (NPm-IMX313) and monomeric NP fused to IMX313T (NPm-IMX313T).

FIG. 8: Comparison of IgG antibody responses, measured by ELISA using recombinant NP, to plasmids encoding NP, monomeric NP (NPm), monomeric NP fused to IMX313 (NPm-IMX313) and monomeric NP fused to IMX313T (NPm-IMX313T).

FIG. 9: Comparison of IgG antibody subclass responses, measured using recombinant NP, to plasmids encoding NP, monomeric NP (NPm), monomeric NP fused to IMX313 (NPm-IMX313) and monomeric NP fused to IMX313T (NPm-IMX313T).

FIG. 10: Influence of the secretion, by the tPA signal peptide, on the various NP fusion proteins. Total T cells were measured by IFNγ ELISpots comparing NP, secreted NP (tPA-NP), secreted monomeric NP (tPA-NPm), secreted NP fused to IMX313 (tPA-NP-IMX313), secreted monomeric NP fused to IMX313 (tPA-NPm-IMX313), and secreted monomeric NP fused to IMX313T (tPA-NPm-IMX313T).

FIG. 11: Influence of the secretion, by the tPA signal peptide, on the CD8+ and CD4+ responses to various NP fusion proteins, measured by IFNγ ELISpots comparing: NP, secreted NP (tPA-NP), secreted monomeric NP (tPA-NPm), secreted NP fused to IMX313 (tPA-NP-IMX313), secreted monomeric NP fused to IMX313 (tPA-NPm-IMX313), and secreted monomeric NP fused to IMX313T (tPA-NPm-IMX313T).

FIG. 12: Influence of the secretion, by the tPA signal peptide, on the IgG responses to various NP fusion proteins, measured by ELISAs comparing: NP, secreted NP (tPA-NP), secreted monomeric NP (tPA-NPm), secreted NP fused to IMX313 (tPA-NP-IMX313), secreted monomeric NP fused to IMX313 (tPA-NPm-IMX313), and secreted monomeric NP fused to IMX313T (tPA-NPm-IMX313T).

FIG. 13: Influence of the secretion, by the tPA signal peptide, on the IgG subclass responses to various NP fusion proteins, measured by ELISAs comparing: NP, secreted NP (tPA-NP), secreted monomeric NP (tPA-NPm), secreted NP fused to IMX313 (tPA-NP-IMX313), secreted monomeric NP fused to IMX313 (tPA-NPm-IMX313), and secreted monomeric NP fused to IMX313T (tPA-NPm-IMX313T).

FIG. 14: Fusion of nucleoprotein to IMX313T increases the immunogenicity of NP to the same extent as the formulation of NP in the oil-in-water adjuvant AddaVax (Invivogen); and the use of AddaVax with the NPm-IMX313T fusion protein shows a synergistic effect.

FIG. 15: Analysis of the results shown in FIG. 14 after separation of CD4 and CD8 cells. The synergistic effect of AddaVax with the NPm-IMX313T protein is seen both in CD4 responses and the CD8 responses.

FIG. 16: IgG responses to nucleoprotein. Fusion of nucleoprotein to IMX313T, in the absence of the adjuvant AddaVax, showed no significant change in IgG titres compared to NP. But in the presence of AddaVax, the fusion protein is significantly more immunogenic than the nucleoprotein.

FIG. 17: Comparison of IgG antibody subclass responses, measured using recombinant NP, following immunization with NP or NPm-IMX313T, with or without AddaVax. As seen in Table 4, NP, with or without Addavax, induced a Th1 response. But the fusion protein NPm-IMX313T, with or without AddaVax, further polarized the IgG response towards Th1.

FIG. 18: SDS-PAGE analysis of the recombinant proteins used for immunisations. Lane 1: molecular weight markers (New England Biolabs); lane 2: recombinant NP (Imgenex); lane 3: purified NP; lane 4: purified NPm-IMX313T.

FIG. 19: SDS-PAGE analysis of the recombinant NPm-IMX313P proteins. Lane 1: purified NP; lane 2: purified NPm-IMX313T; lane 3: purified NPm-IMX313P; lane 4: molecular weight markers (New England Biolabs).

FIG. 20: IgG responses to Protamine or to IMX313P, after immunization of mice with IMX313P protein. This shows that, although the mice produce IgG antibodies to IMX313P (and some cross-react with IMX313), no antibodies which cross-react with protamine were found.

EXAMPLES

For DNA vaccinations, the parent plasmid pcDNA3-NP, as shown in FIG. 1, was modified as described in the Examples below. The plasmids pIMX494 and pIMX497 are described in the patent application PCT/EP2013/076289 filed on Dec. 11, 2013.

Example 1

Insertion of IMX313 into NP Encoding Plasmids

The IMX313 coding sequence was amplified from the plasmid pIMX494 using the oligonucleotide primers IMX1289 (5' caatgcagaggagtacgacaatggatccaagaagcaaggtgatgctgatg 3'—SEQ ID NO: 10) and IMX1290 (5' GTAGAAACAAGGGTATTTTTCTTtattactccttgctcagtccttgc 3'—SEQ ID NO: 11) and inserted into the plasmid pcDNA3-NP as described by Geiser.

Example 2

Insertion of the tPA Signal Peptide

The tPA signal peptide was amplified from the vector pSG2-85A (Spencer) using the oligonucleotides IMX1305 (5' cactgagtgacatcaaaatcatgGATGCAATGAAGAGAGGGC 3'—SEQ ID NO: 12) and IMX1306 (5' cgtaagaccgtttggtgccttggctagctcttctgaatcgggcatggatttcc 3'—SEQ ID NO: 13) and inserted in-frame with the N-terminus of the NP coding sequence in a number of plasmids as described by Geiser.

Example 3

Creation of Two Point Mutations of NP to Render it Monomeric

The oligonucleotide primers IMX1287 (5' ccattctgccgcatttgCagatctaagag 3'—SEQ ID NO: 14) and IMX1288 (5'

CAAAAGGGAGATTTGCCTGTACTGAGAAC 3'—SEQ ID NO: 15) were used to amplify an internal fragment of the NP gene, and the resulting PCR product was inserted into NP-encoding plasmids as described by Geiser. Because both oligonucleotides were imperfectly matched to the NP gene, the insertion of the PCR product generated two point mutations. The IMX1287 primer created the mutation E339A (GAA to GCA), whereas the IMX1288 primer created the mutation R416A in the NP gene (AGA to GCA).

Example 4

Insertion of IMX313T

The IMX313T coding sequence was amplified from the plasmid pIMX497 using the oligonucleotide primers IMX1289 (SEQ ID NO: 10) and IMX051 (5' GTAGAAACAAGGGTATTTTTCTTtattaggagcgacggcgacgc 3'—SEQ ID NO: 16) and inserted into the various pcDNA3-NP-derived plasmids as described by Geiser.

Example 5

DNA Immunizations with the Nucleic Acids According to the Invention 5.1. Protocol Groups of five female BALB/C mice were immunized intramuscularly twice, 14 days apart, with various plasmid DNAs, using 20 g of each plasmid per injection. Immune responses were measured on day 28, to determine the influence of various modifications: +/−IMX313 or IMX313T; +/−the tPA signal peptide; +/−the monomerizing mutations.

Antigen-specific T-cell responses were measured by ELISPOTs, using splenocytes, on day 28. Purified spleen CD4+, CD8+ and Total T cells isolated from the immunized mice were co-cultured with NP A Influenza peptide (amino acids 366-374) purchased from Eurogentec.

ELISPOT Assays: Flat-bottomed, 96-well nitrocellulose plates (Millititer; Millipore) were coated with IFN-γ mAb (15 μg/ml; MABTECH, Stockholm) and incubated overnight at 4° C. After washing with PBS, plates were blocked with 10% fetal bovine serum for one hour at 37° C. $2\times10^6$ cells per well were stimulated with relevant peptides at a final concentration of 2 μg/ml (NP A Influenza peptide) on IPVH-membranes coated with 15 g/ml anti-human IFN− and incubated for 20 hours. After incubation, the plates were washed thoroughly with PBS to remove cells, and IFN− mAb (1 g/ml of biotin, MABTECH) was added to each well. After incubation for 2 h at 37° C., plates were washed and developed with streptavidin-HRP (1 g/ml; MABTECH) for one hour at room temperature. After washing, the substrate (3-amino-9-ethycarbazol (Sigma)) was added and incubated for 15 minutes. After further washing, the red spots were counted under the microscope.

To study the humoral immune responses, we evaluated the antibody levels by ELISAs specific for total IgG, and separately for IgG1 and IgG2a to evaluate the relative proportions of Th1 and Th2. BALB/c mice typically respond to influenza vaccines with a Th2-type immune response, which is associated with the stimulation of IgG1 antibodies. However, the major antibody isotype present in the sera of mice that survive viral infections is IgG2a, which is stimulated during Th1-type immune responses (Huber). Stimulation of IgG2a antibodies has been associated with increased efficacy of influenza vaccination.

For the ELISAs, antigens were diluted to a concentration of 5 mg/ml in 0.1 M sodium carbonate/bicarbonate (pH 9.6) and were then used to coat the wells of MaxiSorb plates (Nunc-Immulon, Denmark). Twofold serial dilutions of the test sera were added to the wells, and following washing, bound antibodies were detected with anti-mouse IgG, or anti-mouse IgG1 or anti-mouse IgG2a (Sigma) conjugated to horseradish peroxidase. Absorbance at 490 nm was determined after o-phenylenediamine (Sigma) and $H_2O_2$ were added; the reactions were stopped with 1 M sulphuric acid.

Results are shown in FIGS. 2 to 5.

5.2. In preliminary experiments, we tested total T cell responses to NP induced by DNA vaccines encoding either NP or NP fused to IMX313. Total T cells isolated from the NP-IMX313 immunized mice showed significantly higher IFN responses compared with those of the NP immunized mice and confirmed the ability of IMX313 to increase T cell responses.

FIG. 2 shows that fusing the parental NP antigen gene to the IMX313 gene improves T cell responses to NP, even when the fusion protein is expressed in the cytosol.

5.3. To determine whether the IFN− detected in the ELISPOTs was produced by CD4 or CD8 T cells, we purified spleen CD4+ and CD8+ T cells from the immunized mice, and these were co-cultured with an Influenza A NP peptide. A significant increase in IFN− production from CD8+ T cells was detected in the group immunized with NP-IMX313. The percentage of antigen-specific CD8+ cells producing IFN− was higher than the corresponding population of CD4+ T (FIG. 3).

FIG. 3 shows that fusing the NP antigen gene to the IMX313 gene improves both CD4+ and CD8+ responses to the NP antigen.

5.4. We then examined the antibody response to NP after immunization and 14 days after the last immunization, NP-specific IgG Ab responses were measured in sera. NP control mice and mice given NP-IMX313 showed moderate NP-specific IgG Abs (FIG. 4), which were higher in the group immunized with NP-IMX313.

FIG. 4 shows that fusing the NP gene to the IMX313 gene improves IgG antibody responses to the NP antigen.

5.5. Sera were also examined for the presence of NP-specific IgG1 and IgG2a antibodies (representative of Th2 and Th1 types of response in Balb/C mice, respectively). NP-specific IgG1 and IgG2a antibody isotypes were detected in the sera of the NP-IMX313 immunized mice; however serum samples from mice given NP alone showed only low levels of IgG1 and IgG2a Ab (FIG. 5).

FIG. 5 shows the subclass distributions of the antibodies induced against the NP antigen. Fusion to the IMX313 gene improved the IgG2A response more than the IgG1 response, converting a Th2-biased response against NP to a Th1-biased response against NP-IMX313.

The results are tabulated here:

TABLE 1

| Immunogenic Component | IgG2a Subclass | IgG1 Subclass | IgG2a/IgG1 | Th pattern |
|---|---|---|---|---|
| NP | 0.215 | 0.265 | 0.8 | Th2 |
| NP-IMX313 | 0.528 | 0.35 | 1.51 | Th1 |

FIG. 6 shows that monomerisation of NP (NPm) improves its immunogenicity slightly (although the improvement is not statistically significant: NS); that NPm immunogenicity is further improved by fusion to the IMX313 gene; and finally that fusing the monomeric NP to the IMX313T gene further enhances NP immunogenicity. Surprisingly, monomerisation of NP does not decrease its immunogenicity.

Figure 1:
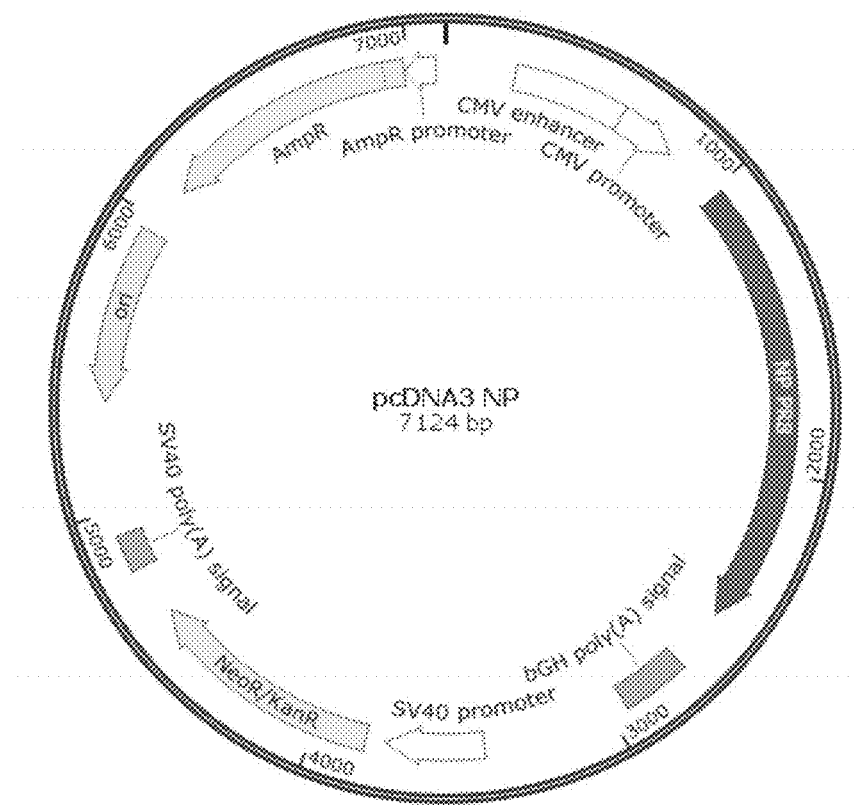
Figure 2:
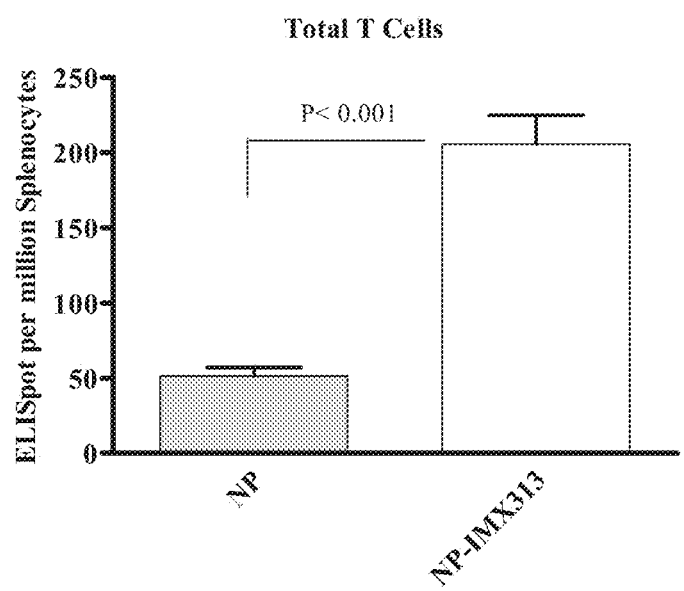
Figure 3:
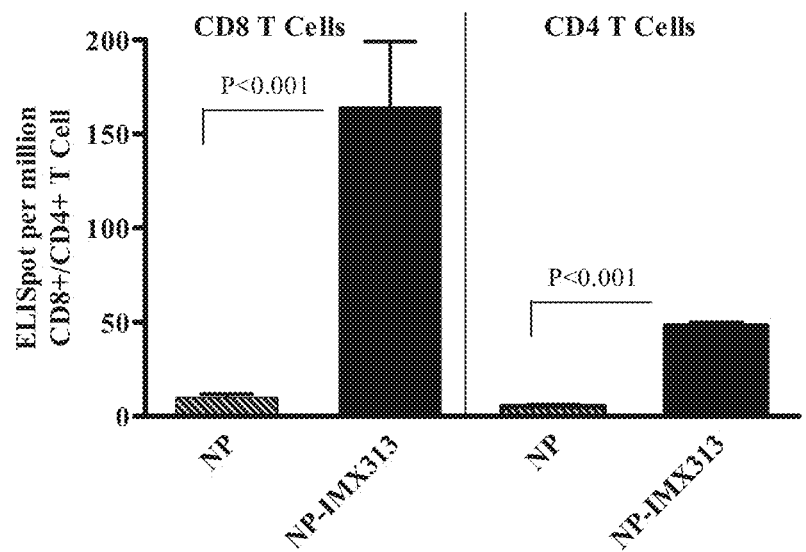
Figure 4:
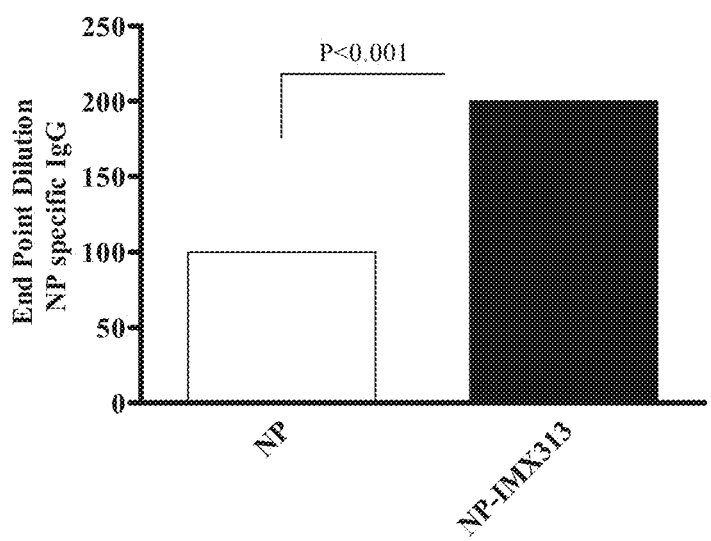
Figure 5:
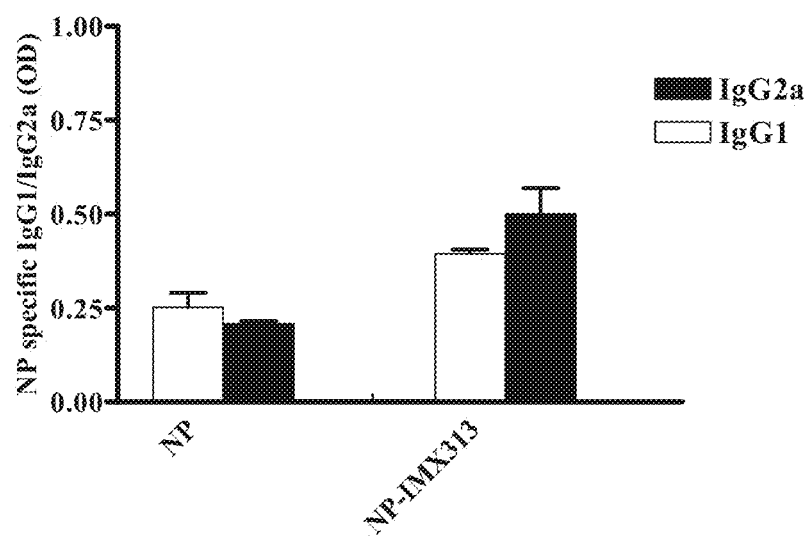
Figure 6:
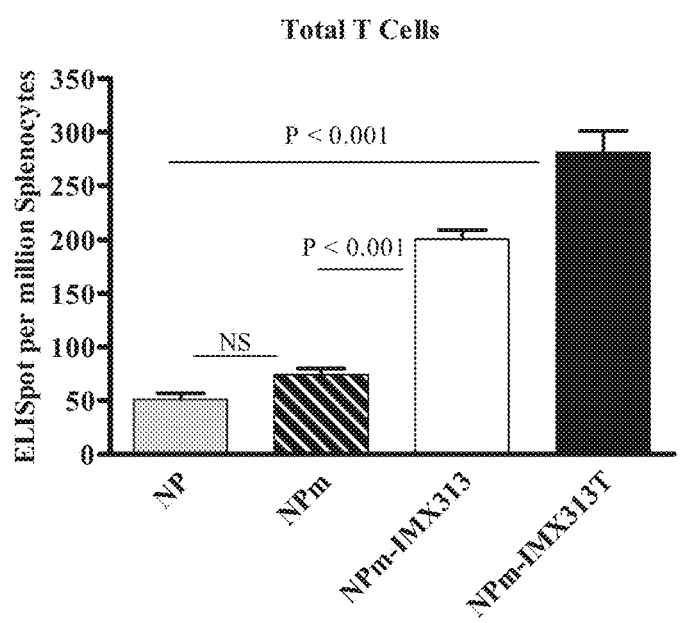
Figure 7:
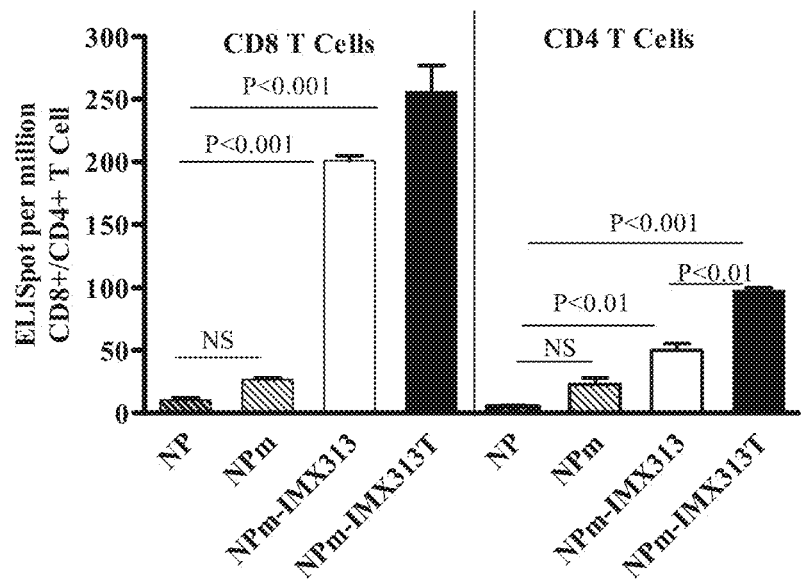
FIG. 7 shows that, on analysis of the CD4+ and CD8+ responses, the same rank ordering as in FIG. 6 is seen: monomerisation of NP improves NP's immunogenicity slightly but not significantly (NS); NP's immunogenicity is further improved by fusion to the IMX313 gene, but that the largest improvement in NP immunogenicity is obtained by fusing the monomeric NP to the IMX313T gene.
Figure 8:
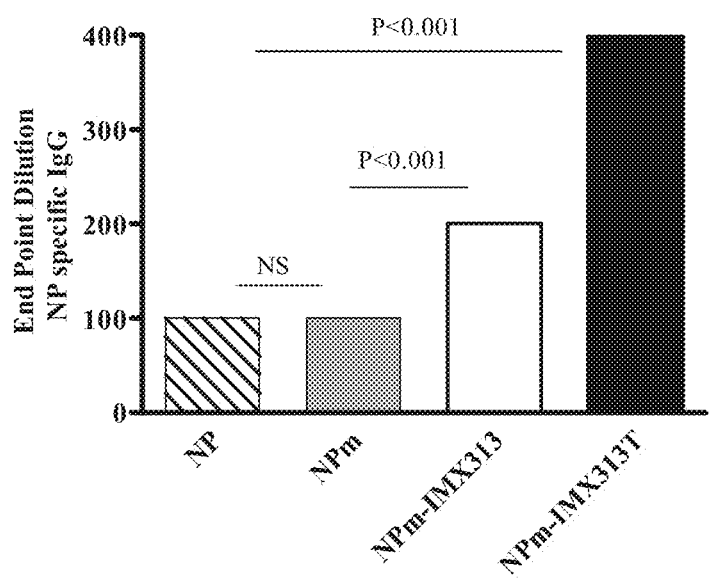
FIG. 8 shows that the same rank ordering is seen for B cell responses as was seen for T cell responses (both CD4+ and CD8+) in FIGS. 6 and 7. Total IgG responses against NP were higher with IMX313T than with IMX313.
Figure 9:
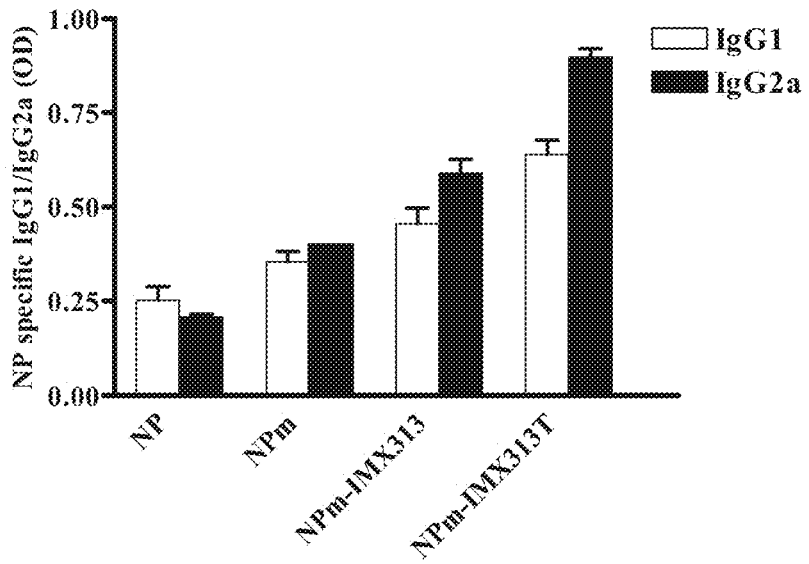

FIG. 9 shows the subclass distributions of the antibodies induced by the monomeric NP antigen. As with NP, fusion to the IMX313 gene augmented the IgG2A responses more than the IgG1 responses, converting a Th2-biased response against NP (0.8) to a Th1-biased response against NP-IMX313 (1.51). This reversal of a Th2 to a Th1 bias maintained by fusion to IMX313T rather than to IMX313 (1.5). Expression of IgG2a antibodies in the influenza vaccines is correlated with clearance of virus and increased protection against lethal influenza challenge. Increased induction of both antibody isotypes as measured by ELISA was a better correlate for vaccine efficacy than neutralization alone (Huber).

TABLE 2

| Immunogenic Component | IgG2a Subclass | IgG1 Subclass | IgG2a/IgG1 | Th pattern |
|---|---|---|---|---|
| NP | 0.215 | 0.265 | 0.8 | Th2 |
| NPm | 0.4 | 0.363 | 1.1 | Th1 |
| NPm-IMX313 | 0.528 | 0.35 | 1.51 | Th1 |
| NPm-IMX313T | 0.95 | 0.632 | 1.5 | Th1 |

Example 6

Secretion of the NP Antigen Improved its Immunogenicity

A series of NP DNA vaccine constructs containing the tissue plasminogen activator (tPA) secretory signal sequence was made: tPA-NP, tPA-NPm, tPA-NPm-IMX313, and tPA-NPm-IMX313T. The effects of the fusion of tPA to NP on the humoral and cellular immune responses from the immunized animals were analyzed.

Mice immunized with tPA containing constructs showed significantly higher IFN responses compared with those of the NP immunized mice and confirmed the ability of IMX313T and the monomerizing mutations to increase T cell responses.

Figure 10:
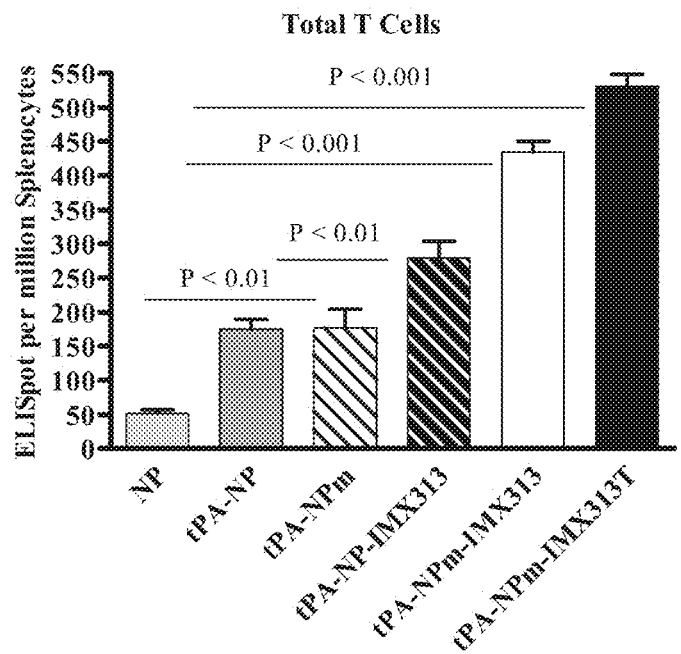

FIG. 10 shows that forcing the secretion of the NP antigen improved its immunogenicity (NP versus tPA-NP), whether it was monomeric or not (tPA-NP versus tPA-NPm). However, fusion to IMX313 showed that use of a monomeric version of NP was more immunogenic than use of the unmodified antigen (tPA-NP-IMX313 versus tPA-NPm-IMX313). And substitution of IMX313 by IMX313T further improved the immunogenicity of NP (tPA-NPm-IMX313 versus tPA-NPm-IMX313T).

Figure 11:
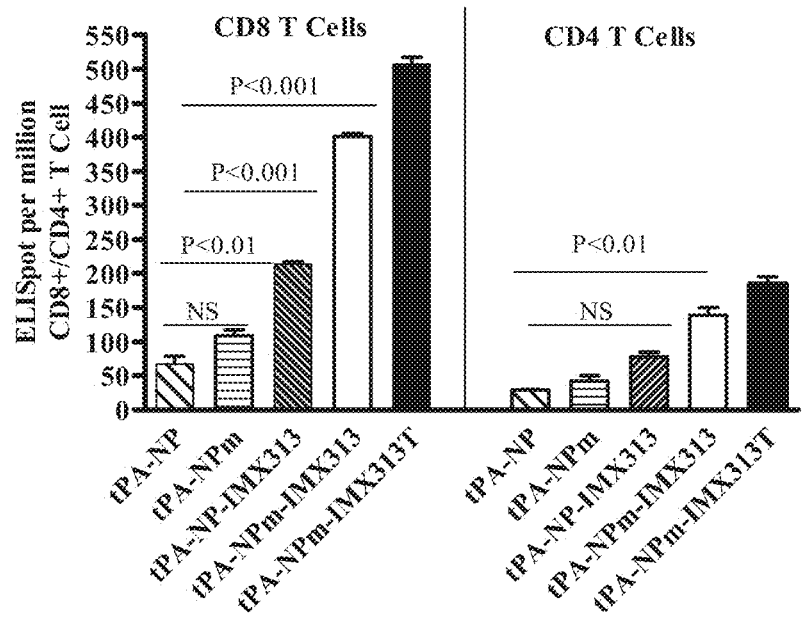

FIG. 11 shows the CD8+ and CD4+ responses to the different secreted versions of NP. The same rank ordering as in FIG. 10 is seen, and the utility of monomerising the antigen is once again pronounced when IMX313 is added. As in the preceding Figures, the largest immune responses are seen when IMX313T is used rather than IMX313.

Figure 12:
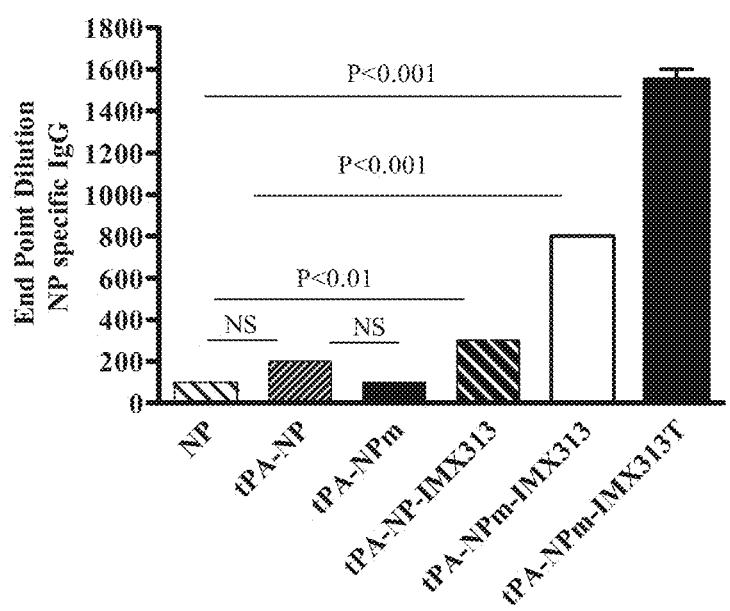

FIG. 12 shows the total IgG responses to the antigen NP and invites the same conclusions as FIG. 11 for T cell responses: the largest responses are seen when IMX313T is used, but secretion (NP versus tPA-NP) and monomerisation (tPA-NP-IMX313 versus tPA-NPm-IMX313) are also important contributions.

Mice immunized with NP alone (as NP, tPA-NP or tPA-NPm) had no or very low levels of anti-NP IgG antibody in their sera (FIG. 12) Mice immunized with tPA-NP-IMX313, tPA-NPm-IMX313 or tPA-NPm-IMX313T on the other hand, showed high levels of systemic NP-specific IgG antibody responses; once again, the tPA-NPm-IMX313T immunized mice had significantly higher (p<0.001) IgG antibody responses compared to all the other groups of immunized mice. This shows that the combination of all the modifications (monomerizing mutations, tPA and IMX313T) confers a significantly improved immunogenicity to the antigen compared to the parental sequence or other combinations.

Figure 13:
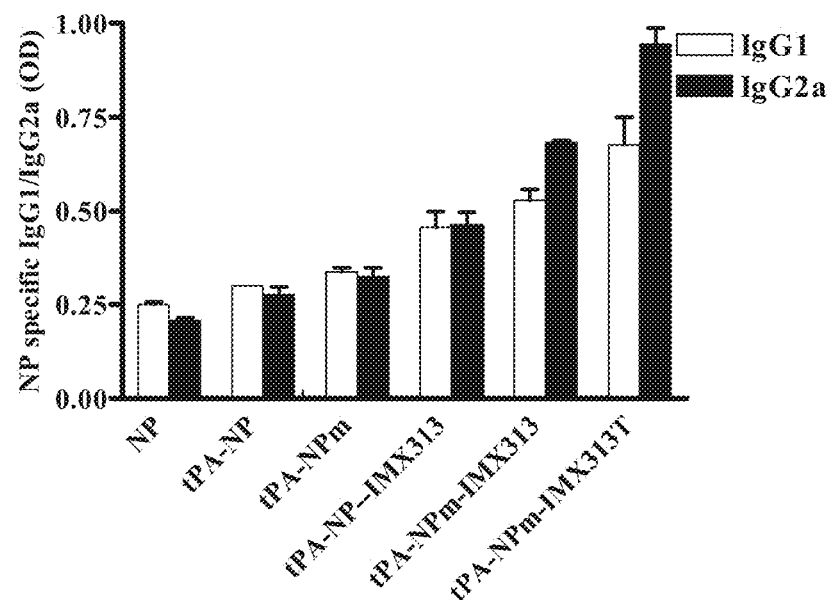
Figure 14:
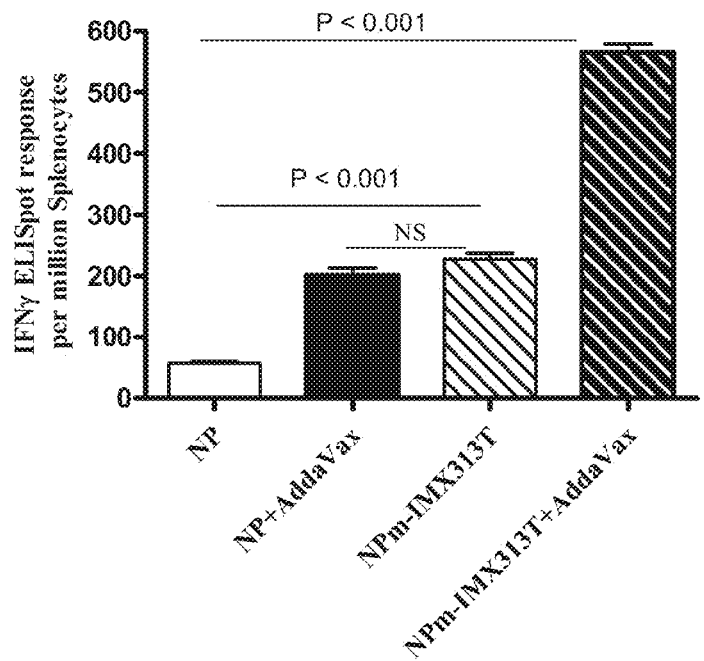
Figure 15:
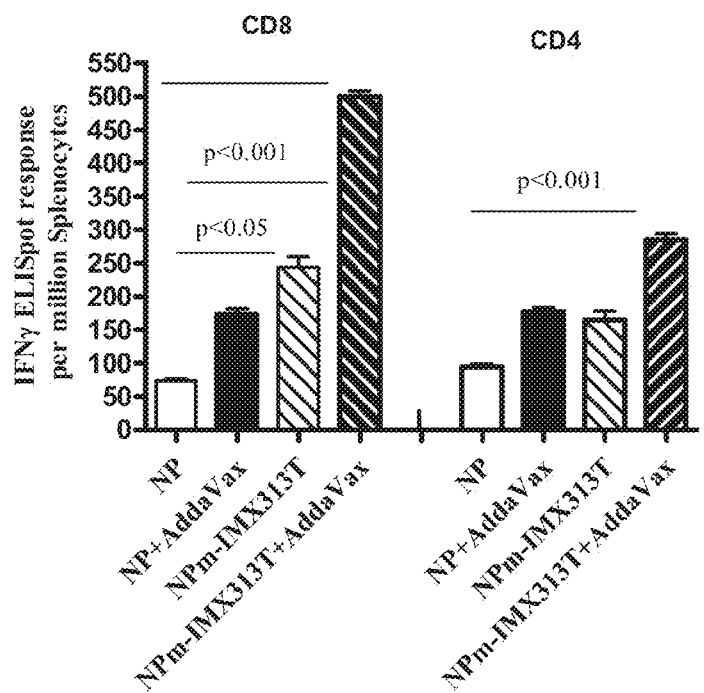
Figure 16:
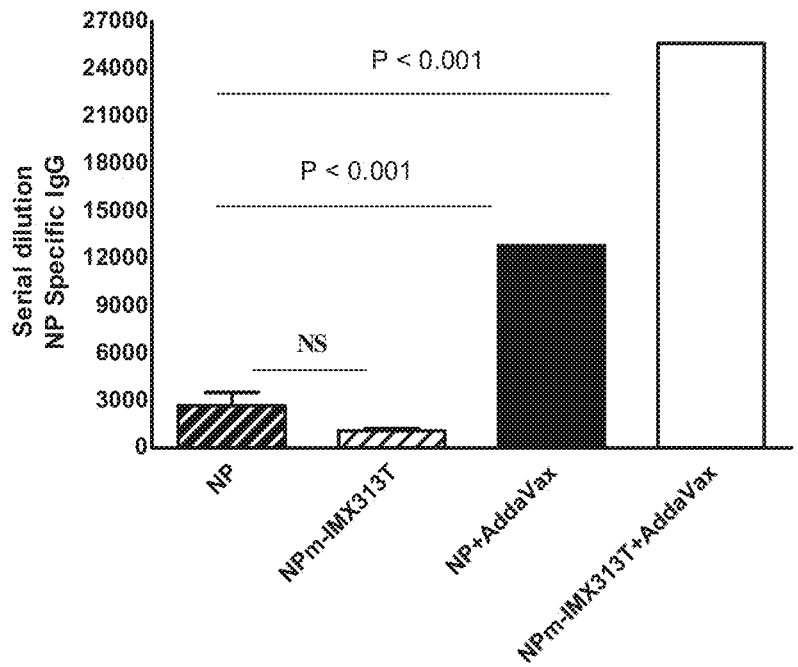
Figure 17:
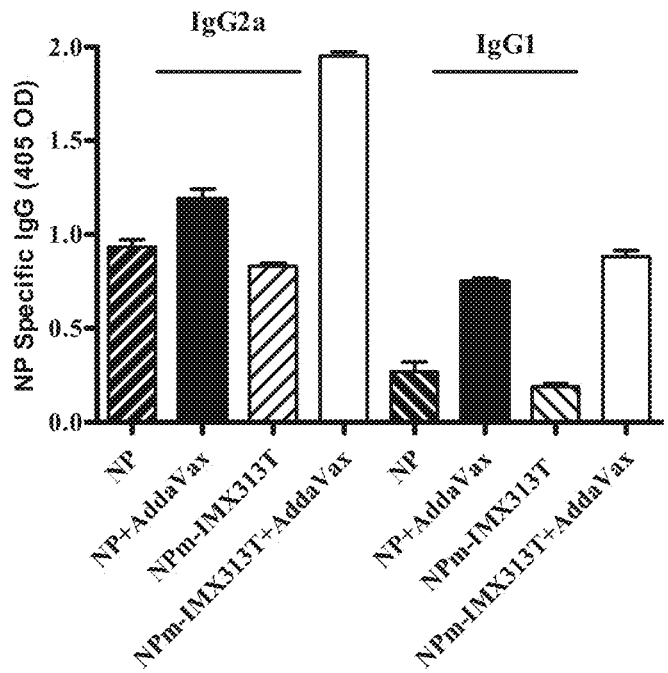
Figure 18:

FIG. 13 shows the subclass analysis of the B cell responses to NP, and illustrates that the initial Th2 bias with NP alone is reversed by IMX313 and by IMX313T. While secretion has little effect on its own (NP versus tPA-NP), monomerisation (tPA-NP-IMX313 versus tPA-NPm-IMX313) and then the replacement of IMX313 by IMX313T (tPA-NPm-IMX313 versus tPA-NPm-IMX313T) all contribute to the improved Th1 (IgG2a) versus Th2 (IgG1) responses.

It is very important that tPA-NPm-IMX313T on its own improves almost equivalently Th1 and Th2 responses. Fusion of NP to IMX313 shows that both Th1 and Th2 responses are both increased, and there is no significant shift in the type of response. But with IMX313T and the monomerizing mutations combined, the Th1 response (IgG2a) starts to predominate. The consensus among immunologists is that Th1 responses are preferable to Th2 responses (FIG. 13).

These results are tabulated here:

TABLE 3

| Immunogenic Component | IgG2a Subclass | IgG1 Subclass | IgG2a/IgG1 | Th pattern |
|---|---|---|---|---|
| NP | 0.215 | 0.265 | 0.8 | Th2 |
| tPA-NP | 0.27 | 0.31 | 0.85 | Th2 |
| tPA-NPm | 0.328 | 0.363 | 0.9 | Th2 |
| tPA-NPm-IMX313 | 0.528 | 0.35 | 1.51 | Th1 |
| tPA-NPm-IMX313T | 0.95 | 0.632 | 1.5 | Th1 |

Example 7

Production of Recombinant NPm-IMX313T Protein

A pET22-derived plasmid expressing the wild-type H1N1 NP protein of strain A/WSN/33 (Tarus 2012b) with a C-terminal 6-His-tag was expressed in the bacterial strain C43R. This strain was made by transforming C43(DE3) with the rare codon expressing plasmid pRARE2 (Novagen). Expression was induced with IPTG in TB (terrific broth) medium. The overexpressed protein was purified initially as described by Ye and by Tarus for the clarification and ion-exchange steps, but in a final step the fusion protein was purified by affinity on Heparin Sepharose, and by gel filtration (Hi Prep 26/60 Sephacryl S-300) as described in the patent application PCT/EP2013/076289 filed on Dec. 11, 2013.

To express the NPm-IMX313T protein, the plasmid expressing NP was modified in two steps. First, the monomerizing mutations were introduced as in Example 3, using the oligonucleotide primers IMX1287 (5' ccattctgccgcatttg-Cagatctaagag 3'—SEQ ID NO: 14) and IMX1288 (5' CAAAAGGGAGATTTGCCTGTACTGAGAAC 3'—SEQ ID NO: 15). In a second step, the 6-His-tag was replaced by the IMX313T coding sequence, using the same oligonucleotide primers as in Example 4: IMX1289 (SEQ ID NO: 10) and IMX051 (5' GTAGAAACAAGGGTATTTTTCTTtatt-aggagcgacggcgacgc 3'—SEQ ID NO: 16). The PCR product was then inserted in place of the 6-His-tag as described by Geiser.

The NPm-IMX313T fusion protein was expressed in the same manner and strain as the NP protein, and purified using the same chromatographic steps.

Example 8

Immunisations

Immunisations of mice were then performed to compare the immunogenicity of NPm-IMX313T, with or without formulation with the AddaVax adjuvant (Invivogen). NP protein, with or without formulation with the AddaVax adjuvant, was used as a control.

To this end, 4 groups of (five) female BALB/c mice were immunized subcutaneously twice, with a 14 day interval, using 20 µg of each protein per injection. The induction of antigen-specific T-cell responses were measured by ELISPOTs, using splenocytes, on day 28. Purified spleen CD4+, CD8+ and Total T cells isolated from the immunized mice were co-cultured with NP protein or Influenza A NP (366-374) peptide. Pre-immune and day 28 antibody responses were measured by ELISAs with NP as antigen.

Example 9

IMX313T is not Degraded by Proteases on Passage Through Secretion Pathways

The results obtained by DNA immunizations with plasmids containing IMX313T strongly suggest that the tail of the molecule is not cleaved by proteases as it passes through the secretion pathway, where proteases are abundant. To examine this question more directly, transfection of CHO K1 cells was undertaken with the pcDNA3 plasmid used to express NPm-IMX313T in vivo. The transfection was carried out as described elsewhere (Krammer).

Eighteen to twenty-four hours later, the supernatants of the transfected cells were recovered by centrifugation, and filtered before being loaded onto a Heparin Sepharose column, as described in the patent application PCT/EP2013/076289 filed on Dec. 11, 2013.

A small "peak C" was seen which proved on SDS-PAGE and Western Blotting to contain the protein NPm-IMX313T.

Example 10

Production of Recombinant NPm-IMX313P Protein

Figure 19:
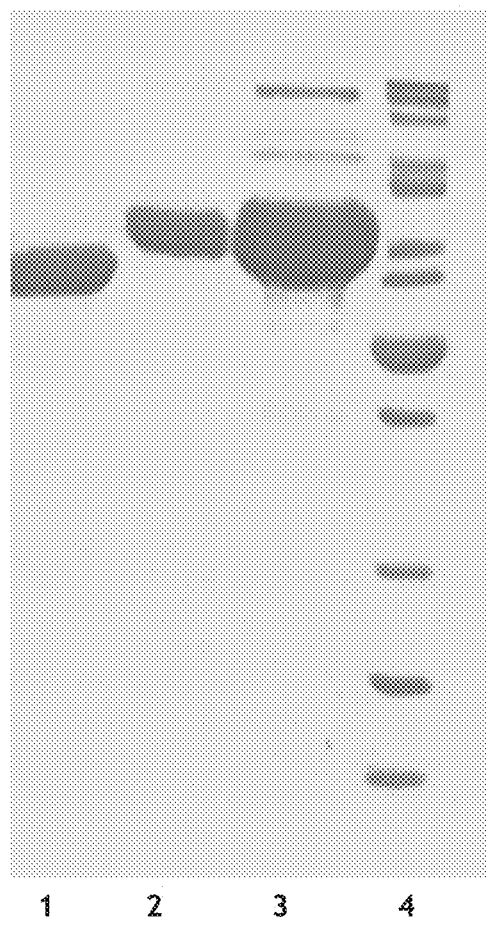

To express the NPm-IMX313P protein, the plasmid expressing NPm-IMX313T was modified by substituting the IMX313P gene in place of the IMX313T gene, by exchanging a restriction fragment (Pml I-Hind III) from a plasmid encoding IMX313P in place of the corresponding fragment in the plasmid encoding the NPM-IMX313T protein. Then the fusion protein was expressed and purified as in Example 7. FIG. 19 shows the purified protein; the principal band is the monomer, but oligomeric forms are also visible (on the overloaded gel) above the principal band.

Example 11

Production of Hyperimmune Antisera to IMX313P

A group of five female BALB/C mice were immunized intramuscularly six times, at 14 day intervals, with the IMX313P protein using 50 µg per injection.

Sera were tested for IgG antibodies by using a modified ELISA method. Protamine sulfate Grade X (Sigma), IMX313 or IMX313P were used to coat the wells of the microplate to capture antibodies. The detection antibodies were goat-anti-mouse IgG-HRP (Sigma), which was reacted with hydrogen peroxide to produce the absorbance readings at 405 nm.

Figure 20:
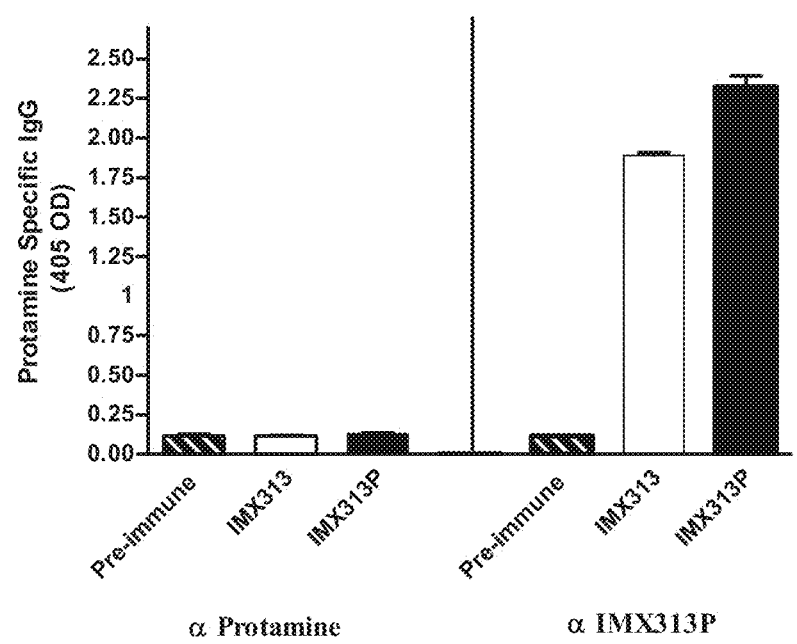

All sera of mice immunized with IMX313P exhibited high titers of IgG antibodies to IMX313P, and some antibodies which cross-reacted with IMX313; but none cross-reacted with Protamine (FIG. 20).

REFERENCES IN ALPHABETICAL ORDER

Akira S, Uematsu S, Takeuchi O. 2006. Pathogen recognition and innate immunity. *Cell* 124:783-801.
Altstein A D, Gitelman A K, Smirnov Y A, Piskareva L M, Zakharova L G, Pashvykina G V, Shmarov M M, Zhirnov O P, Varich N P, Ilyinskii P O, Shneider A M. (2006) Immunization with influenza A NP-expressing vaccinia virus recombinant protects mice against experimental infection with human and avian influenza viruses. *Arch Virol.* 151:921-931.
Antrobus R D, Lillie P J, Berthoud T K, Spencer A J, McLaren J E, Ladell K, Lambe T, Milicic A, Price D A, Hill A V, Gilbert S C. (2012) A T cell-inducing influenza vaccine for the elderly: safety and immunogenicity of MVA-NP+M1 in adults aged over 50 years. PLoS One. 7:e48322.
Arranz R, Coloma R, Chichón F J, Conesa J J, Carrascosa J L, Valpuesta J M, Ortín J, Martín-Benito J. (2012) The structure of native influenza virion ribonucleoproteins. *Science.* 338:1634-1637.
Bachmann M F, Rohrer U H, Kündig T M, Bürki K, Hengartner H, Zinkernagel R M. (1993) The influence of antigen organization on B cell responsiveness. *Science* 262:1448-1451.
Berthoud T K, Hamill M, Lillie P J, Hwenda L, Collins K A, Ewer K J, Milicic A, Poyntz H C, Lambe T, Fletcher H A, Hill A V, Gilbert S C. (2011) Potent CD8+ T-cell immunogenicity in humans of a novel heterosubtypic influenza A vaccine, MVA-NP+M1. *Clin Infect Dis.* 52:1-7.
Blasius A L & Beutler B. 2010. Intracellular Toll-like Receptors. *Immunity* 32:305-315.
Couch R B, Atmar R L, Franco L M, Quarles J M, Niño D, Wells J M, Arden N, Cheung S, Belmont J W. (2012) Prior infections with seasonal influenza A/H1N1 virus reduced the illness severity and epidemic intensity of pandemic H1N1 influenza in healthy adults. *Clin Infect Dis.* 54:311-317.
Epstein S L, Stack A, Misplon J A, Lo C Y, Mostowski H, Bennink J, Subbarao K. (2000) Vaccination with DNA encoding internal proteins of influenza virus does not require CD8(+) cytotoxic T lymphocytes: either CD4(+) or CD8(+) T cells can promote survival and recovery after challenge. *Int Immunol.* 12:91-101.
Epstein S L, Tumpey T M, Misplon J A, Lo C Y, Cooper L A, Subbarao K, Renshaw M, Sambhara S, Katz J M. (2002). DNA vaccine expressing conserved influenza virus proteins protective against H5N1 challenge infection in mice. *Emerg Infect Dis.* 8:796-801.

Fiers W, Neirynck S, Deroo T, Saelens X, Jou W M. (2001) Soluble recombinant influenza vaccines. *Philos Trans R Soc Lond B Biol Sci.* 356:1961-1963.

Fodor E, Devenish L, Engelhardt O G, Palese P, Brownlee G G, García-Sastre A. (1999) Rescue of influenza A virus from recombinant DNA. *J Virol.* 73:9679-9682.

Gammelin M, Altmüller A, Reinhardt U, Mandler J, Harley V R, Hudson P J, Fitch W M, Scholtissek C. (1990) Phylogenetic analysis of nucleoproteins suggests that human influenza A viruses emerged from a 19th-century avian ancestor. *Mol Biol Evol.* 7:194-200.

Geiser M, Cèbe R; Drewello D, Schmitz R. 2001. Integration of PCR fragments at any specific site within cloning vectors without the use of restriction enzymes and DNA ligase. *Biotechniques* 31:88-92.

Gorman O T, Bean W J, Kawaoka Y, Donatelli I, Guo Y J, Webster R G. (1991) Evolution of influenza A virus nucleoprotein genes: implications for the origins of H1N1 human and classical swine viruses. *J Virol.* 65:3704-3714.

Greenland J R, Letvin N L. (2007) Chemical adjuvants for plasmid DNA vaccines. *Vaccine* 25:3731-3741.

Gschoesser C, Almanzar G, Hainz U, Ortin J, Schonitzer D, Schild H, Saurwein-Teissl M, Grubeck-Loebenstein B. (2002). CD4+ and CD8+ mediated cellular immune response to recombinant influenza nucleoprotein. *Vaccine* 20:3731-3738.

Huang B, Wang W, Li R, Wang X, Jiang T, Qi X, Gao Y, Tan W, Ruan L. (2012) Influenza A virus nucleoprotein derived from *Escherichia coli* or recombinant vaccinia (Tiantan) virus elicits robust cross-protection in mice. *Virol J.* 9:322.

Huber V C, McKeon R M, Brackin M N, Miller L, Keating R, Brown S A, Makarova N, Perez D R, MacDonald G H, McCullers J A. (2006) Distinct Contributions of Vaccine-Induced Immunoglobulin G1 (IgG1) and IgG2a Antibodies to Protective Immunity against Influenza. *CLINICAL AND VACCINE IMMUNOLOGY* 13: 981-990.

Krammer F, Pontiller J, Tauer C, Palmberger D, Maccani A, Baumann M, Grabherr R. (2010) Evaluation of the influenza A replicon for transient expression of recombinant proteins in mammalian cells. *PLoS One.* 5:e13265.

Laddy D J, Yan J, Kutzler M, Kobasa D, Kobinger G P, Khan A S, Greenhouse J, Sardesai N Y, Draghia-Akli R, Weiner D B. (2008) Heterosubtypic protection against pathogenic human and avian influenza viruses via in vivo electroporation of synthetic consensus DNA antigens. *PLoS One.* 3:e2517.

Lamb R A, Krug R M. Orthomyxoviridae: the viruses and their replication. In: Knipe D M, Howley P M, editors., eds. Fields Virology Vol 1 4th ed. Philadelphia, Pa.: Lippincott Williams & Wilkins; 2001:1487-1531.

Lillie P J, Berthoud T K, Powell T J, Lambe T, Mullarkey C, Spencer A J, Hamill M, Peng Y, Blais M E, Duncan C J, Sheehy S H, Havelock T, Faust S N, Williams R L, Gilbert A, Oxford J, Dong T, Hill A V, Gilbert S C. (2012) Preliminary assessment of the efficacy of a T-cell-based influenza vaccine, MVA-NP+M1, in humans. *Clin Infect Dis.* 55:19-25.

Luo M, Tao P, Li J, Zhou S, Guo D, Pan Z. (2008) Immunization with plasmid DNA encoding influenza A virus nucleoprotein fused to a tissue plasminogen activator signal sequence elicits strong immune responses and protection against H5N1 challenge in mice. *J Virol Methods.* 154:121-127.

Mbawuike I, Zang Y, Couch R B. (2007) Humoral and cell-mediated immune responses of humans to inactivated influenza vaccine with or without QS21 adjuvant. *Vaccine* 25:3263-3269.

McMichael A J, Gotch F M, Dongworth D W, Clark A, Potter C W. (1983a) Declining T-cell immunity to influenza, 1977-82. *Lancet* 2(8353):762-724.

McMichael A J, Gotch F M, Noble G R, Beare P A. (1983b) Cytotoxic T-cell immunity to influenza. *N Engl J Med.* 309:13-17.

McMichael A J, Michie C A, Gotch F M, Smith G L, Moss B. (1986) Recognition of influenza A virus nucleoprotein by human cytotoxic T lymphocytes. *J Gen Virol.* 67:719-726.

Moeller A, Kirchdoerfer R N, Potter C S, Carragher B, Wilson I A. (2012) Organization of the influenza virus replication machinery. *Science* 338:1631-1634.

Nakada S, Creager R S, Krystal M, Palese P. (1984) Complete nucleotide sequence of the influenza C/California/78 virus nucleoprotein gene. *Virus Res.* 1:433-441.

Ogun S A, Dumon-Seignovert L, Marchand J B, Holder A A, Hill F. (2008). The oligomerization domain of C4-binding protein (C4bp) acts as an adjuvant, and the fusion protein comprised of the 19-kilodalton merozoite surface protein 1 fused with the murine C4bp domain protects mice against malaria. *Infect Immun.* 76:3817-3823.

Roy S, Kobingerb G P, Lina J, Figueredoa J, Calcedoa R, Kobasab D, Wilson J M. (2007) Partial protection against H5N1 influenza in mice with a single dose of a chimpanzee adenovirus vector expressing nucleoprotein. *Vaccine* 25:6845-6851.

Schotsaert M, Ysenbaert T, Neyt K, Ibañez L I, Bogaert P, Schepens B, Lambrecht B N, Fiers W, Saelens X. (2012) Natural and long-lasting cellular immune responses against influenza in the M2e-immune host. *Mucosal Immunology* 1-12.

Spencer A J, Hill F, Honeycutt J D, Cottingham M G, Bregu M, Rollier C S, Furze J, Draper S J, Søgaard K C, Gilbert S C, Wyllie D H, Hill A V. (2012) Fusion of the *Mycobacterium tuberculosis* antigen 85A to an oligomerization domain enhances its immunogenicity in both mice and non-human primates. *PLoS One.* 7:e33555.

Staneková Z, Varečlová E. (2010) Conserved epitopes of influenza A virus inducing protective immunity and their prospects for universal vaccine development. *Virology* 7:351

Sullivan S M, Doukas J, Hartikka J, Smith L, Rolland A. (2010) Vaxfectin: a versatile adjuvant for plasmid DNA- and protein-based vaccines. *Expert Opin Drug Deliv.* 7:1433-1446.

Sutter G, Wyatt L S, Foley P L, Bennink J R, Moss B. (1994) A recombinant vector derived from the host range-restricted and highly attenuated MVA strain of vaccinia virus stimulates protective immunity in mice to influenza virus. *Vaccine* 12:1032-1040.

Tarus B, Bakowiez O, Chenavas S, Duchemin L, Estrozi L F, Bourdieu C, Lejal N, Bernard J, Moudjou M, Chevalier C, Delmas B, Ruigrok R W, Di Primo C, Slama-Schwok A. (2012a) Oligomerization paths of the nucleoprotein of influenza A virus. *Biochimie.* 94:776-785.

Tarus B, Chevalier C, Richard C A, Delmas B, Di Primo C, Slama-Schwok A. (2012b) Molecular dynamics studies of the nucleoprotein of influenza A virus: role of the protein flexibility in RNA binding. *PLoS One.* 7:e30038.

Thomas P G, Keating R, Hulse-Post D J, and Doherty P C. (2006) Cell-mediated Protection in Influenza Infection. *Emerging Infectious Diseases* 12: 48-54.

Ulmer J B, Donnelly J J, Parker S E, Rhodes G H, Felgner P L, Dwarki V J, Gromkowski S H, Deck R R, DeWitt C M, Friedman A, et al. (1993) Heterologous protection against influenza by injection of DNA encoding a viral protein. *Science.* 259:1745-1749.

Wraith D C, Vessey A E, Askonas B A. (1987) Purified influenza virus nucleoprotein protects mice from lethal infection. *J Gen Virol.* 68:433-440.

Xu J, Christman M C, Donis R O, Lu G. (2011) Evolutionary dynamics of influenza A nucleoprotein (NP) lineages revealed by large-scale sequence analyses. *Infect Genet Evol.* 11:2125-2132.

Ye Q, Guu T S, Mata D A, Kuo R L, Smith B, Krug R M, Tao Y J. (2012) Biochemical and structural evidence in support of a coherent model for the formation of the double-helical influenza A virus ribonucleoprotein. *MBio.* 4:e00467-12.

Ye Q, Krug R M, Tao Y J. (2006) The mechanism by which influenza A virus nucleoprotein forms oligomers and binds RNA. *Nature.* 444:1078-1082.

Yewdell J W, Bennink J R, Smith G L, Moss B. (1985) Influenza A virus nucleoprotein is a major target antigen for cross-reactive anti-influenza A virus cytotoxic T lymphocytes. *Proc Natl Acad Sci USA.* 82:1785-1789.

The invention claimed is:

1. A fusion protein comprising at least one variant of the nucleoprotein antigen (NP) and a variant of the carrier protein of sequence SEQ ID NO: 1 comprising a C-terminal substitution of at least one positively-charged peptide having the sequence ZXBBBBZ (SEQ ID NO: 3) wherein (i) Z is any amino acid or is absent, (ii) X is any amino acid and (iii) B is an arginine (R) or a lysine (K).

2. The fusion protein according to claim 1 wherein the nucleoprotein antigen is a monomeric antigen.

3. The fusion protein according to claim 1 wherein the at least one nucleoprotein antigen is from an Influenza strain A, B or C.

4. The fusion protein according to claim 3 wherein the monomeric nucleoprotein antigen is encoded by the sequence SEQ ID NO: 2.

5. The fusion protein according to claim 1 wherein the variant of the carrier protein is the sequence SEQ ID NO: 4 or SEQ ID NO: 5.

6. The fusion protein according to claim 2 wherein the at least one nucleoprotein antigen is from an Influenza strain A, B or C.

7. The fusion protein according to claim 3 wherein the variant of the carrier protein is the sequence SEQ ID NO: 4 or SEQ ID NO: 5.

8. The fusion protein according to claim 1, wherein the NP antigen comprises a signal peptide.

9. A method for inducing an immune response against influenza disease in a human or animal in need thereof, comprising administering in said human or animal bodies an immunogenic composition comprising:
a fusion protein comprising at least one variant of the nucleoprotein antigen (NP) and a variant of the carrier protein of sequence SEQ ID NO: 1 comprising a C-terminal substitution of at least one positively-charged peptide having the sequence ZXBBBBZ (SEQ ID NO: 3) wherein (i) Z is any amino acid or is absent, (ii) X is any amino acid and (iii) B is an arginine (R) or a lysine (K), and
a vaccine adjuvant.

10. The method according to claim 9, wherein said nucleoprotein antigen (NP) is a monomeric antigen.

11. An immunogenic composition comprising:
a fusion protein comprising at least one variant of the nucleoprotein antigen (NP) and a variant of the carrier protein of sequence SEQ ID NO: 1 comprising a C-terminal substitution of at least one positively-charged peptide having the sequence ZXBBBBZ (SEQ ID NO: 3) wherein (i) Z is any amino acid or is absent, (ii) X is any amino acid and (iii) B is an arginine (R) or a lysine (K), and
a vaccine adjuvant.

12. The immunogenic composition of claim 11, wherein the adjuvant is nucleic acid ligands for intracellular TLRs.

13. The immunogenic composition of claim 12 wherein the nucleic acid ligands for intracellular TLRs are poly I:C.

14. A method for increasing T-cell immunogenicity of the nucleoprotein antigen (NP) in a human or animal, comprising administering in said human or animal bodies an immunogenic composition comprising:
a fusion protein comprising at least one variant of the nucleoprotein antigen (NP) and a variant of the carrier protein of sequence SEQ ID NO: 1 comprising a C-terminal substitution of at least one positively-charged peptide having the sequence ZXBBBBZ (SEQ ID NO: 3) wherein (i) Z is any amino acid or is absent, (ii) X is any amino acid and (iii) B is an arginine (R) or a lysine (K), and
a vaccine adjuvant.

15. The method according to claim 14, wherein said nucleoprotein antigen (NP) is a monomeric antigen.

* * * * *

SEQUENCE LISTING

```
<160> NUMBER OF SEQ ID NOS: 16

<210> SEQ ID NO 1
<211> LENGTH: 55
<212> TYPE: PRT
<213> ORGANISM: Artificial Sequence
<220> FEATURE:
<223> OTHER INFORMATION: IMX313

<400> SEQUENCE: 1

Lys Lys Gln Gly Asp Ala Asp Val Cys Gly Glu Val Ala Tyr Ile Gln
1               5                   10                  15

Ser Val Val Ser Asp Cys His Val Pro Thr Ala Glu Leu Arg Thr Leu
            20                  25                  30

Leu Glu Ile Arg Lys Leu Phe Leu Glu Ile Gln Lys Leu Lys Val Glu
        35                  40                  45

Leu Gln Gly Leu Ser Lys Glu
    50                  55

<210> SEQ ID NO 2
<211> LENGTH: 497
<212> TYPE: PRT
<213> ORGANISM: Artificial Sequence
<220> FEATURE:
<223> OTHER INFORMATION: monomeric NP

<400> SEQUENCE: 2

Ala Thr Lys Gly Thr Lys Arg Ser Tyr Glu Gln Met Glu Thr Asp Gly
1               5                   10                  15

Glu Arg Gln Asn Ala Thr Glu Ile Arg Ala Ser Val Gly Lys Met Ile
            20                  25                  30

Asp Gly Ile Gly Arg Phe Tyr Ile Gln Met Cys Thr Glu Leu Lys Leu
        35                  40                  45

Ser Asp Tyr Glu Gly Arg Leu Ile Gln Asn Ser Leu Thr Ile Glu Arg
    50                  55                  60

Met Val Leu Ser Ala Phe Asp Glu Arg Arg Asn Lys Tyr Leu Glu Glu
65                  70                  75                  80

His Pro Ser Ala Gly Lys Asp Pro Lys Lys Thr Gly Gly Pro Ile Tyr
                85                  90                  95

Arg Arg Val Asp Gly Lys Trp Arg Arg Glu Leu Ile Leu Tyr Asp Lys
            100                 105                 110

Glu Glu Ile Arg Arg Ile Trp Arg Gln Ala Asn Asn Gly Asp Asp Ala
        115                 120                 125

Thr Ala Gly Leu Thr His Met Met Ile Trp His Ser Asn Leu Asn Asp
    130                 135                 140

Ala Thr Tyr Gln Arg Thr Arg Ala Leu Val Arg Thr Gly Met Asp Pro
145                 150                 155                 160
```

```
Arg Met Cys Ser Leu Met Gln Gly Ser Thr Leu Pro Arg Arg Ser Gly
                165                 170                 175

Ala Ala Gly Ala Ala Val Lys Gly Val Gly Thr Met Val Met Glu Leu
            180                 185                 190

Ile Arg Met Ile Lys Arg Gly Ile Asn Asp Arg Asn Phe Trp Arg Gly
        195                 200                 205

Glu Asn Gly Arg Arg Thr Arg Ile Ala Tyr Glu Arg Met Cys Asn Ile
    210                 215                 220

Leu Lys Gly Lys Phe Gln Thr Ala Ala Gln Arg Thr Met Val Asp Gln
225                 230                 235                 240

Val Arg Glu Ser Arg Asn Pro Gly Asn Ala Phe Glu Asp Leu Ile
                245                 250                 255

Phe Leu Ala Arg Ser Ala Leu Ile Leu Arg Gly Ser Val Ala His Lys
                260                 265                 270

Ser Cys Leu Pro Ala Cys Val Tyr Gly Ser Ala Val Ala Ser Gly Tyr
                275                 280                 285

Asp Phe Glu Arg Glu Gly Tyr Ser Leu Val Gly Ile Asp Pro Phe Arg
        290                 295                 300

Leu Leu Gln Asn Ser Gln Val Tyr Ser Leu Ile Arg Pro Asn Glu Asn
305                 310                 315                 320

Pro Ala His Lys Ser Gln Leu Val Trp Met Ala Cys His Ser Ala Ala
                325                 330                 335

Phe Ala Asp Leu Arg Val Ser Ser Phe Ile Arg Gly Thr Lys Val Val
                340                 345                 350

Pro Arg Gly Lys Leu Ser Thr Arg Gly Val Gln Ile Ala Ser Asn Glu
            355                 360                 365

Asn Met Glu Thr Met Glu Ser Ser Thr Leu Glu Leu Arg Ser Arg Tyr
        370                 375                 380

Trp Ala Ile Arg Thr Arg Ser Gly Gly Asn Thr Asn Gln Gln Arg Ala
385                 390                 395                 400

Ser Ser Gly Gln Ile Ser Ile Gln Pro Thr Phe Ser Val Gln Ala Asn
                405                 410                 415

Leu Pro Phe Asp Arg Pro Thr Ile Met Ala Ala Phe Thr Gly Asn Thr
                420                 425                 430

Glu Gly Arg Thr Ser Asp Met Arg Thr Glu Ile Ile Arg Leu Met Glu
            435                 440                 445

Ser Ala Arg Pro Glu Asp Val Ser Phe Gln Gly Arg Gly Val Phe Glu
        450                 455                 460

Leu Ser Asp Glu Lys Ala Thr Ser Pro Ile Val Pro Ser Phe Asp Met
465                 470                 475                 480

Ser Asn Glu Gly Ser Tyr Phe Phe Gly Asp Asn Ala Glu Glu Tyr Asp
                485                 490                 495

Asn

<210> SEQ ID NO 3
<211> LENGTH: 7
<212> TYPE: PRT
<213> ORGANISM: Artificial Sequence
<220> FEATURE:
<223> OTHER INFORMATION: positively-charged peptide
<220> FEATURE:
<221> NAME/KEY: MISC_FEATURE
<222> LOCATION: (1)..(1)
<223> OTHER INFORMATION: Xaa is any amino acid or is absent
<220> FEATURE:
<221> NAME/KEY: MISC_FEATURE
```

```
<222> LOCATION: (2)..(2)
<223> OTHER INFORMATION: Xaa is any amino acid
<220> FEATURE:
<221> NAME/KEY: MISC_FEATURE
<222> LOCATION: (3)..(6)
<223> OTHER INFORMATION: Xaa is arginine (R) or lysine (K)
<220> FEATURE:
<221> NAME/KEY: MISC_FEATURE
<222> LOCATION: (7)..(7)
<223> OTHER INFORMATION: Xaa is any amino acid or is absent

<400> SEQUENCE: 3

Xaa Xaa Xaa Xaa Xaa Xaa Xaa
1               5

<210> SEQ ID NO 4
<211> LENGTH: 57
<212> TYPE: PRT
<213> ORGANISM: Artificial Sequence
<220> FEATURE:
<223> OTHER INFORMATION: IMX313T

<400> SEQUENCE: 4

Lys Lys Gln Gly Asp Ala Asp Val Cys Gly Glu Val Ala Tyr Ile Gln
1               5                   10                  15

Ser Val Val Ser Asp Cys His Val Pro Thr Ala Glu Leu Arg Thr Leu
            20                  25                  30

Leu Glu Ile Arg Lys Leu Phe Leu Glu Ile Gln Lys Leu Lys Val Glu
        35                  40                  45

Leu Gln Ser Pro Arg Arg Arg Ser
    50                  55

<210> SEQ ID NO 5
<211> LENGTH: 55
<212> TYPE: PRT
<213> ORGANISM: Artificial Sequence
<220> FEATURE:
<223> OTHER INFORMATION: IMX313P

<400> SEQUENCE: 5

Lys Lys Gln Gly Asp Ala Asp Val Cys Gly Glu Val Ala Tyr Ile Gln
1               5                   10                  15

Ser Val Val Ser Asp Cys His Val Pro Thr Ala Glu Leu Arg Thr Leu
            20                  25                  30

Leu Glu Ile Arg Lys Leu Phe Leu Glu Ile Gln Lys Leu Lys Val Glu
        35                  40                  45

Gly Arg Arg Arg Arg Arg Ser
    50                  55

<210> SEQ ID NO 6
<211> LENGTH: 1767
<212> TYPE: DNA
<213> ORGANISM: Artificial Sequence
<220> FEATURE:
<223> OTHER INFORMATION: Gene encoding tPA-NPm-IMX313T

<400> SEQUENCE: 6
atggatgcaa tgaagagagg gctctgctgt gtgctgctgc tgtgtggagc agtcttcgtt      60
tcgcccagcc aggaaatcca tgcccgattc agaagagcta gccaaggcac caaacggtct    120
tacgaacaga tggagactga tggagaacgc cagaatgcca ctgaaatcag agcatccgtc    180
ggaaaaatga ttggtggaat tggacgattc tacatccaaa tgtgcacaga acttaaactc    240
agtgattatg agggacggtt gatccaaaac agcttaacaa tagagagaat ggtgctctct    300
```

-continued

```
gcttttgacg aaaggagaaa taaatacctg gaagaacatc ccagtgcggg gaaagatcct    360
aagaaaactg gaggacctat atacagaaga gtaaacggaa agtggatgag agaactcatc    420
ctttatgaca aagaagaaat aaggcgaatc tggcgccaag ctaataatgg tgacgatgca    480
acggctggtc tgactcacat gatgatctgg cattccaatt tgaatgatgc aacttatcag    540
aggacaaggg ctcttgttcg caccggaatg gatcccagga tgtgctctct gatgcaaggt    600
tcaactctcc ctaggaggtc tggagccgca ggtgctgcag tcaaaggagt tggaacaatg    660
gtgatggaat tggtcaggat gatcaaacgt gggatcaatg atcggaactt ctggaggggt    720
gagaatggac gaaaaacaag aattgcttat gaaagaatgt gcaacattct caaagggaaa    780
tttcaaactg ctgcacaaaa agcaatgatg gatcaagtga gagagagccg gaacccaggg    840
aatgctgagt tcgaagatct cacttttcta gcacggtctg cactcatatt gagagggtcg    900
gttgctcaca agtcctgcct gcctgcctgt gtgtatggac ctgccgtagc cagtgggtac    960
gactttgaaa gagagggata ctctctagtc ggaatagacc ctttcagact gcttcaaaac   1020
agccaagtgt acagcctaat cagaccaaat gagaatccag cacacaagag tcaactggtg   1080
tggatggcat gccattctgc cgcatttgca gatctaagag tattgagctt catcaaaggg   1140
acgaaggtgg tcccaagagg gaagctttcc actagaggag ttcaaattgc ttccaatgaa   1200
aatatggaga ctatggaatc aagtacactt gaactgagaa gcaggtactg ggccataagg   1260
accagaagtg gaggaaacac caatcaacag agggcatctg cgggccaaat cagcatacaa   1320
cctacgttct cagtacaggc aaatctccct tttgacagaa caaccgttat ggcagcattc   1380
actgggaata cagaggggag aacatctgac atgaggaccg aaatcataag gatgatggaa   1440
agtgcaagac cagaagatgt gtctttccag gggcggggag tcttcgagct ctcggacgaa   1500
aaggcagcga gcccgatcgt gccttccttt gacatgagta atgaaggatc ttatttcttc   1560
ggagacaatg cagaggagta cgacaatgga tccaagaagc aaggtgatgc tgatgtgtgc   1620
ggagaggttg cttatattca gagcgtcgtc tccgattgcc acgtgcctac agcggaactg   1680
cgtactctgc tggaaatacg aaaactcttc ctggagattc aaaaactgaa ggtggaactg   1740
cagtctccgc gtcgccgtcg ctcctaa                                       1767
```

<210> SEQ ID NO 7
<211> LENGTH: 1761
<212> TYPE: DNA
<213> ORGANISM: Artificial Sequence
<220> FEATURE:
<223> OTHER INFORMATION: Gene encoding tPA-NPm-IMX313P

<400> SEQUENCE: 7

```
atggatgcaa tgaagagagg gctctgctgt gtgctgctgc tgtgtggagc agtcttcgtt     60
tcgcccagcc aggaaatcca tgcccgattc agaagagcta gccaaggcac caaacggtct    120
tacgaacaga tggagactga tggagaacgc cagaatgcca ctgaaatcag agcatccgtc    180
ggaaaaatga ttggtggaat tggacgattc tacatccaaa tgtgcacaga acttaaactc    240
agtgattatg agggacggtt gatccaaaac agcttaacaa tagagagaat ggtgctctct    300
gcttttgacg aaaggagaaa taaatacctg gaagaacatc ccagtgcggg gaaagatcct    360
aagaaaactg gaggacctat atacagaaga gtaaacggaa agtggatgag agaactcatc    420
ctttatgaca aagaagaaat aaggcgaatc tggcgccaag ctaataatgg tgacgatgca    480
acggctggtc tgactcacat gatgatctgg cattccaatt tgaatgatgc aacttatcag    540
```

```
aggacaaggg ctcttgttcg caccggaatg gatcccagga tgtgctctct gatgcaaggt    600
tcaactctcc ctaggaggtc tggagccgca ggtgctgcag tcaaaggagt tggaacaatg    660
gtgatggaat tggtcaggat gatcaaacgt gggatcaatg atcggaactt ctggaggggt    720
gagaatggac gaaaaacaag aattgcttat gaaagaatgt gcaacattct caaagggaaa    780
tttcaaactg ctgcacaaaa agcaatgatg gatcaagtga gagagagccg aacccaggg     840 aatgctgagt tcgaagatct cacttttcta gcacggtctg cactcatatt gagagggtcg    900
gttgctcaca agtcctgcct gcctgcctgt gtgtatggac ctgccgtagc cagtgggtac    960
gactttgaaa gagagggata ctctctagtc ggaatagacc ctttcagact gcttcaaaac   1020
agccaagtgt acagcctaat cagaccaaat gagaatccag cacacaagag tcaactggtg   1080
tggatggcat gccattctgc cgcatttgca gatctaagag tattgagctt catcaaaggg   1140
acgaaggtgg tcccaagagg gaagctttcc actagaggag ttcaaattgc ttccaatgaa   1200
aatatggaga ctatggaatc aagtacactt gaactgagaa gcaggtactg ggccataagg   1260
accagaagtg gaggaaacac caatcaacag agggcatctg cgggccaaat cagcatacaa   1320
cctacgttct cagtacaggc aaatctcccct tttgacagaa caaccgttat ggcagcattc   1380
actgggaata cagaggggag aacatctgac atgaggaccg aaatcataag gatgatggaa   1440
agtgcaagac cagaagatgt gtcttttccag gggcggggag tcttcgagct ctcggacgaa   1500
aaggcagcga gcccgatcgt gccttccttt gacatgagta atgaaggatc ttatttcttc   1560
ggagacaatg cagaggagta cgacaatgga tccaagaagc aaggtgatgc tgatgtgtgc   1620
ggagaggttg cttatattca gagcgtcgtc tccgattgcc acgtgcctac agcggaactg   1680
cgtactctgc tggaaatacg aaaactcttc ctggagattc aaaaactgaa ggtggaaggt   1740
cgccgtcgcc gtcgctccta a                                             1761

<210> SEQ ID NO 8
<211> LENGTH: 39
<212> TYPE: RNA
<213> ORGANISM: Artificial Sequence
<220> FEATURE:
<223> OTHER INFORMATION: ssRNA40
<220> FEATURE:
<221> NAME/KEY: misc_feature
<222> LOCATION: (1)..(39)
<223> OTHER INFORMATION: s is a phosphothiotate linkage

<400> SEQUENCE: 8
gscscscsgs uscsusgsus usgsusgsus gsascsusc                            39

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide ODN1826

<400> SEQUENCE: 9
tccatgacgt tcctgacgtt                                                 20

<210> SEQ ID NO 10
<211> LENGTH: 50
<212> TYPE: DNA
<213> ORGANISM: Artificial Sequence
<220> FEATURE:
<223> OTHER INFORMATION: Oligonucleotide IMX1289

<400> SEQUENCE: 10
```
caatgcagag gagtacgaca atggatccaa gaagcaaggt gatgctgatg        50

<210> SEQ ID NO 11
<211> LENGTH: 47
<212> TYPE: DNA
<213> ORGANISM: Artificial Sequence
<220> FEATURE:
<223> OTHER INFORMATION: Oligonucleotide IMX1290

<400> SEQUENCE: 11
gtagaaacaa gggtattttt ctttattact ccttgctcag tccttgc        47

<210> SEQ ID NO 12
<211> LENGTH: 42
<212> TYPE: DNA
<213> ORGANISM: Artificial Sequence
<220> FEATURE:
<223> OTHER INFORMATION: Oligonucleotide IMX1305

<400> SEQUENCE: 12
cactgagtga catcaaaatc atggatgcaa tgaagagagg gc        42

<210> SEQ ID NO 13
<211> LENGTH: 53
<212> TYPE: DNA
<213> ORGANISM: Artificial Sequence
<220> FEATURE:
<223> OTHER INFORMATION: Oligonucleotide IMX1306

<400> SEQUENCE: 13
cgtaagaccg tttggtgcct tggctagctc ttctgaatcg ggcatggatt tcc        53

<210> SEQ ID NO 14
<211> LENGTH: 29
<212> TYPE: DNA
<213> ORGANISM: Artificial Sequence
<220> FEATURE:
<223> OTHER INFORMATION: Oligonucleotide IMX1287

<400> SEQUENCE: 14
ccattctgcc gcatttgcag atctaagag        29

<210> SEQ ID NO 15
<211> LENGTH: 29
<212> TYPE: DNA
<213> ORGANISM: Artificial Sequence
<220> FEATURE:
<223> OTHER INFORMATION: Oligonucleotide IMX1288

<400> SEQUENCE: 15
caaaagggag atttgcctgt actgagaac        29

<210> SEQ ID NO 16
<211> LENGTH: 44
<212> TYPE: DNA
<213> ORGANISM: Artificial Sequence
<220> FEATURE:
<223> OTHER INFORMATION: Oligonucleotide IMX051

<400> SEQUENCE: 16
gtagaaacaa gggtattttt ctttattagg agcgacggcg acgc        44